US011170295B1

(12) United States Patent
Carmichael et al.

(10) Patent No.: US 11,170,295 B1
(45) Date of Patent: Nov. 9, 2021

(54) SYSTEMS AND METHODS FOR TRAINING A PERSONALIZED MACHINE LEARNING MODEL FOR FALL DETECTION

(71) Applicant: Tidyware, LLC, Bellevue, WA (US)

(72) Inventors: Philip F Carmichael, Bellevue, WA (US); Brian Hayward, Seattle, WA (US); Alvin G Solidum, Bellevue, WA (US); Travis T Okahara, Kirkland, WA (US); William L Richman, Seattle, WA (US); Raman Chandrasekar, Seattle, WA (US); Patrick Dean Kennedy, Fall City, WA (US); Ray Sun, Bellevue, WA (US)

(73) Assignee: Tidyware, LLC, Bellevue, WA (US)

( * ) Notice: Subject to any disclaimer, the term of this patent is extended or adjusted under 35 U.S.C. 154(b) by 1070 days.

(21) Appl. No.: 15/709,059

(22) Filed: Sep. 19, 2017

Related U.S. Application Data

(60) Provisional application No. 62/396,755, filed on Sep. 19, 2016.

(51) Int. Cl.
*G06N 3/08* (2006.01)
*G06N 3/04* (2006.01)

(52) U.S. Cl.
CPC ............. *G06N 3/08* (2013.01); *G06N 3/0445* (2013.01)

(58) Field of Classification Search
CPC ............................... G06N 3/08; G06N 3/0445
See application file for complete search history.

(56) References Cited

PUBLICATIONS

Medrano, Carlos, et al. "The effect of personalization on smartphone-based fall detectors." Sensors 16.1 (2016): 117. (Year: 2016).*
Medrano, Carlos, et al. "Detecting falls as novelties in acceleration patterns acquired with smartphones." PloS one 9.4 (2014): e94811. (Year: 2014).*
Medrano, Carlos, et al. "Personalizable smartphone application for detecting falls." IEEE-EMBS International Conference on Biomedical and Health Informatics (BHI). IEEE, 2014. (Year: 2014).*
Cheffena, Michael. "Fall detection using smartphone audio features." IEEE journal of biomedical and health informatics 20.4 (2015): 1073-1080. (Year: 2015).*
Thompson, Benjamin Berry, et al. "Implicit learning in autoencoder novelty assessment." Proceedings of the 2002 International Joint Conference on Neural Networks. IJCNN'02 (Cat. No. 02CH37290). vol. 3. IEEE, 2002. (Year: 2002).*

(Continued)

*Primary Examiner* — Benjamin P Geib
(74) *Attorney, Agent, or Firm* — DWC Law Firm, P.S.

(57) ABSTRACT

Systems and methods for training a personalized Machine Learning (ML) model used to detect fall events are described herein. The methods may be implemented by one or more computing devices and may include obtaining sensor data associated with one or more activities of a user. A processed or unprocessed version of at least a copy of the sensor data having been fed to a personalized ML model associated with the user and that has been determined not to be associated with a fall event; and using the obtained sensor data training the personalized ML model.

20 Claims, 19 Drawing Sheets

(56) References Cited

PUBLICATIONS

Zhang, Zhong, Christopher Conly, and Vassilis Athitsos. "A survey on vision-based fall detection." Proceedings of the 8th ACM international conference on PErvasive technologies related to assistive environments. 2015. (Year: 2015).*

Bulotta, Simon, et al. "Fall detection using an ensemble of learning machines." Neural Nets and Surroundings. Springer, Berlin, Heidelberg, 2013. 81-90. (Year: 2013).*

\* cited by examiner

*Calculated Features*

- maximum
- mean_abs_change
- absolute_sum_of_changes
- sample_entropy
- binned_entropy
- kurtosis
- agg_autocorrelation
- standard_deviation
- variance
- abs_energy
- range_count
- number_cwt_peaks
- mean_second_derivate_central
- percentage_of_reoccurring_values_to_all_values
- percentage_of_reoccurring_datapoints_to_all_datapoints
- ratio_value_number_to_time_series_length
- count_above_mean
- count_below_mean
- minimum
- mean_change
- has_duplicate
- median
- number_crossing_m
- linear_trend
- large_standard_deviation
- max_langevin_fixed_point
- autocorrelation
- quantile
- friedrich_coefficients
- index_mass_quantile
- approximate_entropy
- augmented_dickey_fuller
- longest_strike_below_mean
- mean sum_values
- c3
- longest_strike_above_mean
- ratio_beyond_r_sigma
- energy_ratio_by_chunks
- ar_coefficient
- skewness spkt_welch_density
- partial_autocorrelation
- cwt_coefficients
- agg_linear_trend
- change_quantiles
- number_peaks
- time_reversal_asymmetry_statistic
- fft_coefficient
- symmetry_looking

| Layer (type) | Output Shape | Param # |
|---|---|---|
| input_1 (InputLayer) | (None, 338) | 0 |
| dense_1 (Fully Connected) | (None, 200) | 67800 |
| dense_2 (Fully Connected) | (None, 100) | 20100 |
| dense_3 (Fully Connected) | (None, 50) | 5050 |
| dense_4 (Fully Connected) | (None, 25) | 1275 |
| dense_5 (Fully Connected) | (None, 50) | 1300 |
| dense_6 (Fully Connected) | (None, 100) | 5100 |
| dense_7 (Fully Connected) | (None, 200) | 20200 |
| dense_8 (Fully Connected) | (None, 338) | 67938 |

Total params: 188,763

SYSTEMS AND METHODS FOR TRAINING A PERSONALIZED MACHINE LEARNING MODEL FOR FALL DETECTION

CROSS REFERENCE TO RELATED APPLICATION(S)

This application claims the benefit of U.S. Provisional Patent Application Ser. No. 62/396,755, filed on Sep. 19, 2016, which is incorporated herein by reference in its entirety.

BACKGROUND

1. Field of the Invention

The present invention relates to event detection, and more particularly to systems and methods for detecting fall events.

2. Description of Related Art

According to the CDC, seniors 65+, more than any other age group, are at risk for falls with 473 per 10,000 men and 767.2 per 10,000 women annually requiring hospital attention due to a fall (Liu, S W. "American Journal of Emergency Medicine", "Frequency of ED revisits and death among older adults after a fall . . . ", 2015). Certain diseases and medical conditions, including Parkinson's and Diabetes also increase the likelihood of falls. The speed at which the effects of a fall can escalate is shocking and can often be measured in mere minutes.

There are now over 80 million people in the United States alone age 55 or older. With the population of adults over age 60 growing, and as life expectancy increases, there are more people living longer. People like having their independence. People want to enjoy life and be free to continue going on adventures, exploring, and, when needed, getting quality healthcare.

Of course, it is not just the elderly who are at risk of slipping, tripping, or falling. For example, many younger people either participate in an active lifestyle (e.g., rock climbing, hiking, etc.) or work in a high-risk occupation (e.g., construction, logger) that exposes them to increased risk for falls.

Whether a person is young and healthy, or elderly and fragile, a slipping, stumbling, or falling accident can lead to serious consequences if a person is unconscious or unable to get up. In fact, sometimes people are not able to help themselves when an accident happens and their lack of ability to communicate their need for help can complicate or make the situation worse.

In order to achieve better outcomes from fall events, there are a number of devices that are currently available designed to assist end users in reporting fall events. For example, there are numerous medical alert devises that permit end users to transmit an alert when they have a fall. Unfortunately, many of these devices require the end user to be conscious and physically able to activate the alert device in order to transmit a medical emergency alert. Further, these devices typically require the end user to be aware that the end user, in fact, has a medical emergency such as a fall, which is not always possible with the elderly, who may be suffering from mental capacity issues such as Alzheimer's or Dementia.

There are also some commercially available systems, which may be in the form of a dedicated device (e.g., a wearable device such as a pendant), or specialized application running on a mobile device (e.g., smartphones) that are claimed to be able to detect fall events. However, such systems have a history of not being very useful due to false alarms. This has been true for both dedicated devices as well as mobile devices executing specialized applications.

Accordingly, there is a need for devices, systems, and methods that can accurately and automatically detect fall events of end users.

SUMMARY

In various embodiments, a computer implemented method for training a personalized machine learning (ML) model for use in detecting fall events of a user, the method includes operations to obtain sensor data associated with one or more activities of the user, the personalized ML model designed to recognize processed sensor data associated with non-fall activities, a copy of the sensor data having been previously processed and the previously processed sensor data having been fed to the personalized ML model, the personalized ML model not recognizing the previously processed sensor data, and the previously processed sensor data having been determined not be associated with a fall event; train the personalized ML model using the sensor data; and provide the trained personalized ML model to determine occurrence of a fall event involving the user.

In some embodiments, the sensor data includes at least accelerometer data or gyroscope data.

In some embodiments, the sensor data includes data from a heart rate monitor, a barometer, an audio sensor, a camera, or a global positioning system (GPS).

In some embodiments, the sensor data is received from a mobile device associated with the user via one or more networks.

In some embodiments, the personalized ML model configured as an autoencoder neural network, a Long Short-Term Memory (LSTM) network, a multiple linear regression model, or a random forest classifier.

In some embodiments, the personalized ML model includes a generalized normal activity ML model generated using activity data of members of a segment of general population and a personalized normal activity ML model generated using activity data of the user collected via one or more sensors, the generalized normal activity ML model and the personalized normal activity ML model being chained together in an ensemble fashion.

In some embodiments, the personalized ML model is generated by combining a generalized normal activity ML model that was generated using activity data of members of a segment of general population and a personalized normal activity ML model that was generated using activity data of the user.

In some embodiments, the operation to train the personalized ML model using the sensor data includes operations to extract relevant data from the sensor data to provide windowed data, calculate feature values on the windowed data, and train the personalized ML model using the calculated feature values.

In some embodiments, the operation to provide the trained personalized ML model includes an operation to transmit the trained personalized ML model to a mobile computer device associated with the user.

In some embodiments, the computer-implemented methods further include operations to detect an anomalous event using the trained personalized ML model; and determine occurrence of a fall event based, at least in part, on the detection of the anomalous event.

In some embodiments, the operation to determine occurrence of a fall event includes an operation to determine that distance traveled towards earth by one or more sensors that provided the sensor data exceeds a threshold distance In some embodiments, the personalized ML model is a personalized normal activity ML model.

In various embodiments, a system is described herein that includes at least one memory configured to store computer-executable instructions; at least one processor configured to access the at least one memory and execute the computer-executable instructions to: obtain sensor data associated with one or more activities of a user, at least a copy of the sensor data having been fed to a personalized ML model of the user, the personalized ML model designed to recognize sensor data associated with non-fall activities of the user, the personalized ML model not recognizing the at least the copy of the sensor data, and the at least the copy of the sensor data having been determined not be associated with a fall event; train the personalized ML model using the sensor data; and provide the trained personalized ML model to facilitate determination of an occurrence of a fall event involving the user.

BRIEF DESCRIPTION OF THE DRAWINGS

FIG. 8B shows a list of feature values that may be calculated for a windowed sensor data according to some embodiments.

DETAILED DESCRIPTION

Figure 1A:
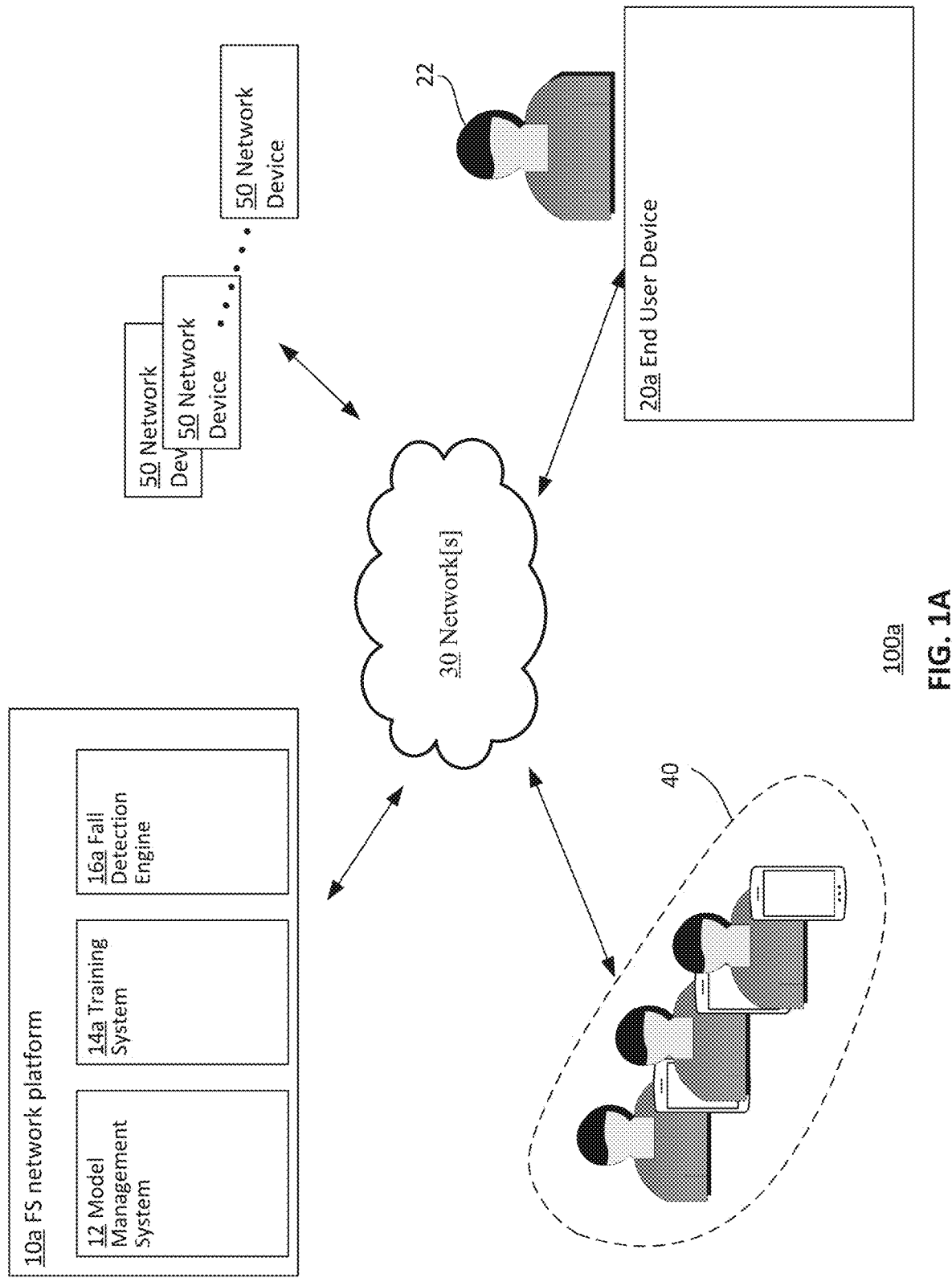
FIG. 1A illustrates an example network according to some embodiments.

In the following description, certain specific details are set forth in order to provide a thorough understanding of various embodiments of the disclosure. However, upon reviewing this disclosure one skilled in the art will understand that the disclosure may be practiced without many of these details. In other instances, well-known structures/apparatus, systems and methods associated with computers, wireless devices, networks/cloud based computing, and SaaS, have not been described in detail to avoid unnecessarily obscuring the descriptions of the embodiments of the disclosure.

Throughout various portions of the following description, the embodiments of the present disclosure are described in the context of application to specific examples as presented. However, these examples are not intended to be limited unless otherwise expressly stated. As will be understood by one skilled in the art after reviewing this disclosure, various embodiments of the present disclosure may have a wide variety of applications in other contexts and fields.

The term, computer readable medium or media, does not include "transitory waves or signals."

Various embodiments of the present disclosure are described in the context of a mobile device such as a smart phone or a wearable computing device executing a specialized software application ("app"); however, all or many of the features described for the various embodiments may be implemented using specialized software on other smart devices, or firmware on any smart device capable of processing data/information, such as, for example, specialized portable (or stationary) hardware carried or worn by a user, having capabilities to receive and process input data/information to generate an output. In some embodiments, a non-transitory computer-readable media has instructions for instructing a smart device for carrying out any of the steps to be described herein.

The drawings submitted herewith include example information depicted for illustrative purposes, and are not intended to be limiting unless otherwise indicated. Also, various examples set forth below may include Fall Safety (FS) systems usable for storing and processing information/data described herein and for executing instructions for carrying out various aspects of the present disclosure. However, as will be appreciated by those skilled in the art, the FS systems may comprise multiple computer devices to provide aggregate processing capacity and storage capacity, either in parallel or in a distributed computing context.

Furthermore, in some embodiments, various embodiments of the present disclosure are delivered via a cloud computing model, so that whenever a network system (e.g., Fall Safety (FS) network platform) is mentioned (e.g., such as in the claims of this application, if any), the network system can include or consist of cloud based type hosting environment. Also, in various embodiments, specialized software applications or application components of the present disclosure may be stored on a remote user computer/system, or mobile device (e.g., smartphone or wearable device such as a smart watch, smart hearing aid, or augmented reality device) to execute various tasks associated with various embodiments of the present disclosure, in conjunction with one or more applications residing on the network system, as will be appreciated by those skilled in the art after reviewing this disclosure. Moreover, the network system may provide software as a service, or may be hosted by an organization using system(s) and method(s) presented herein.

In order to help people who are at risk of falling, systems and methods are provided herein that are able to automatically detect fall events (which could be falls, trips, or slips) of an end user. In various embodiments, the detection of a fall (e.g., "fall event") by an end user may be accomplished by processing, through a personalized "normal activity" Machine Learning (ML) model, data collected by one or more sensors that are monitoring the activities of the end user. The personalized normal activity ML model will be referred to herein as a "personalized ML model" and is a ML model that has been selected and/or trained specifically for that end user. For purposes of this description, the systems and methods may be referred to herein as Fall Safety (FS) systems and methods. In various embodiments, and as will be described in greater detail herein, references to "FS systems" may be in reference to the various systems and sub-systems located at one or more sites of a network that may be employed, in combination, in order to implement the various operations and functions to be described herein.

The one or more sensors used to monitor the activities of an end user may include one or more of a wide variety of sensors including, for example, motion sensors (e.g., accelerometers and gyroscopes) as well as other types of sensors (e.g. heart rate, GPS, camera, barometers, etc.). As will be further described herein, the data collected from one or more sensors monitoring the activities of an end user, in some embodiments, may be processed using advanced signal processing techniques, then fed into a personalized "normal activity" Machine Learning (ML) model to detect (e.g., infer) a fall event. In alternative implementations, data collected from the one or more sensors may be fed directly into the personalized ML model where the personalized ML model processes the sensor data before using the processed sensor data to detect a fall event. In some cases, at least some of the sensor data collected from the one or more sensors that have been determined not to be associated with a fall (i.e., "fall event") of the end user may be used to train the personalized ML model of the end user to provide a more accurate personalized ML model. Note that in various embodiments, the sensor data used to train the personalized ML model may be a copy of the sensor data that was processed and fed or directly fed to the personalized ML model and that was identified as being associated with a non-fall event.

For purposes of the following description references to a "personalized ML model," unless indicated otherwise, may also be in reference to a generic ML model that has been selected for use for detecting a fall event of an end user (hereinafter simply "user"), where the generic ML model is a ML model that has been trained for a specific demographic group from the general population. This is because when a user first begins using the FS systems to detect falls in an automated fashion, there is no true personalized ML model that he can use. Instead, the user starts off by using a generic ML model specifically selected for the user based on identifying the demographic group that the user belongs to. As the user continues to use the FS systems, the FS systems collects sensor data, some of which is used to train the personalized ML model so that the personalized ML model becomes more personalized and more accurate with respect to that user.

To detect a fall event of a particular end user, sensor data that are collected from one or more sensors monitoring the user, such as motion sensor data, may be continuously or semi-continuously collected during the course of a given day. Such data may be collected via a mobile device (e.g., a smartphone or a wearable device such as a smartwatch, pendant, augmented reality device, etc.). The collected sensor data may then be processed and fed to a personalized ML model associated the user, which is able to detect an anomaly in the processed sensor data (i.e., processed sensor data signals). That is, the personalized ML model may be a personalized "normal activity" ML model of the user that is configured to at least recognize processed sensor data (e.g., processed sensor data signal or signals) of normal activities ("non-fall events") of the user. As a result, the personalized ML model is also able to recognize anomalous processed sensor data having signal or data patterns that are not recognizable by the personalized ML model.

For purposes of the following description, the user activity that is associated with the anomalous processed sensor data may be referred to as an "anomalous event." An anomalous event may either be an actual fall event or a non-fall event (that produces processed or unprocessed sensor data that is yet to be recognized by the personalized ML model). Note that for purposes of the following description the word "anomaly," as will be used herein may be in reference to an anomalous processed sensor data not recognized by a personalized ML model or to an anomalous event or activity of a user associated with the personalized ML model and the anomalous processed sensor data. For purposes of the following, non-fall events that are not recognized by the personalized normal activity ML model may also be referred to as a "false alarm" events since such events may initially be flagged as a potential fall event.

For purposes of the following description, a personalized ML model is particular to a specific user and that recognizes processed or unprocessed sensor data associated with non-fall activities of the particular user among other things. Note also that for purposes of the following description, the use of the words "detect," "detecting," or "detection" in connection with fall events may be broadly construed to include "inference" or "inferencing" of fall events. For example, the FS systems and methods according to various embodiments of the present disclosure may employ a neural network, such as anomaly detection neural network (ADNN), to facilitate detection of a fall event. Unfortunately, detection of a fall event by a neural network is, at best, only an inference to a fall event since the only way a detected event can definitively be confirmed as a fall event is to get confirmation by the user (or a third party), which in some cases, may not be possible (e.g., the user is unconscious, disabled, or has mental incapacity such as Dementia). Thus, the use of the words detect, detecting, and/or detection may also mean inference, inferencing, and so forth unless indicated otherwise.

When fed with processed sensor data of the user, the personalized ML model may determine that the processed sensor data has a pattern that it does not recognize and, therefore, recognize it as an anomaly. The event associated with "anomalous" processed sensor data may also be referred to as an anomalous event which may either be a fall event, or a non-fall event (i.e., false alarm event) that is not yet recognized by the personalized ML model as being a non-fall event. As will be further described herein, the anomalous event may be ascertained to be a fall or a non-fall event using various approaches. For example, in some cases, the user may be prompted (e.g., the display of the user's smartphone requesting confirmation of fall or non-fall) to indicate whether the anomalous event was a non-fall event or a fall event. If the user does not respond to the prompt, then the FS systems and methods may in some cases assume that the user is incapacitated and assume that there was, in fact, a fall event and that the user is incapacitated. In other cases, however, if the user does not respond to the prompt within a certain time period, the FS systems and methods may assume that there was no fall-event. This may be the case when, for example, there is an indication that the anonymous event is determined to likely be merely a stumble or slip rather than a true fall event. As will be further described herein, other approaches may be employed to conclude that the anomalous event is in fact, a true fall event or a non-fall event.

If the anomalous event is determined to be a fall event, then certain actions may be executed including alerting emergency contacts. On the other hand, if the anomalous event (e.g., jumping on a trampoline) is determined to be a non-fall event, then the sensor data that caused the personalized ML model to flag the anomalous event may be used to train the personalized ML model so that if the personalized ML model receives the same type of processed or unprocessed sensor data (e.g., processed or unprocessed sensor data signals) with the same processed or unprocessed data pattern, it will recognize the processed or unprocessed sensor data as being associated with a non-fall event. Each time an anomalous event is detected and is ultimately determined to be a non-fall event, the sensor data associated with that non-fall event may be used to train the personalized ML model so that it can more accurately detect fall events. As can be seen, this process may be repeated over and over again to make the personalized ML model a more accurate model for an individual.

To generate a personalized ML model for a particular user, in some embodiments, a generic ML model for a segment of the general population that the user belongs to may be selected for first time use by the user since the user will not have a true personalized ML model. A generic ML model (which is a generic "normal activity" ML model) for a segment of the general population may be created from normal non-fall activities data (e.g., motion data) collected from many members of the same population segment. In some embodiments, multiple generic ML models may be maintained for different segments of the general population. For example, you could maintain one generic ML model for highly active people, one for moderately active people, and one for sedentary people.

One reason why personalized "normal activity" ML models are used to detect fall events rather than a ML model that directly recognizes fall events is because there is usually very little data available related to actual fall events, particularly with respect to specific individual users. That is, fall events are relatively rare, particularly with respect to any specific user. As a result, developing ML models that can directly recognize fall events with high accuracy can be a tall order and difficult to achieve. However, it is usually much easier to collect data associated with everyday activities of users. Thus, by developing a precise personalized "normal activity" ML model, fall events can be detected or at least inferred simply by looking for anomalies from the normal activity ML model.

According to various embodiments, in order to accurately detect (e.g., infer) that a user has fallen, data provided by one or more sensors (e.g., motion sensors such as accelerometer and/or gyroscope, barometer, GPS, heart rate sensor, etc.) monitoring the activities of the user may be collected. Fortunately, many of these sensors used to monitor the activities of the user can be found in mobile devices (e.g., smart devices and wearable devices). The raw data collected from these sensors may then be processed using advanced signal processing techniques and then fed into a personalized ML model of the user to detect anomalous events that are not recognized by the personalized ML model as being a non-fall event (e.g., movements associated with normal activities of the user) or a fall event. If the anomalous event is determined to be a non-fall event (e.g., by the end user confirming that it is a false alarm and is a non-fall) then the associated sensor data may be used to update or train the personalized ML model so that if the same anomalous event is encountered again, the personalized ML model will recognize it (or recognize at least the processed sensor data associated with the anomalous event) as a non-fall event. On the other hand, if the anomalous event is determined to be a fall event (e.g., such as the end user not responding to a prompt confirming that it was a false alarm) then the FS systems are designed to automatically alert emergency contacts (e.g., 9-1-1 services, doctors, relatives, so forth) with, in some cases, an option to cancel the alert.

Figure 4:
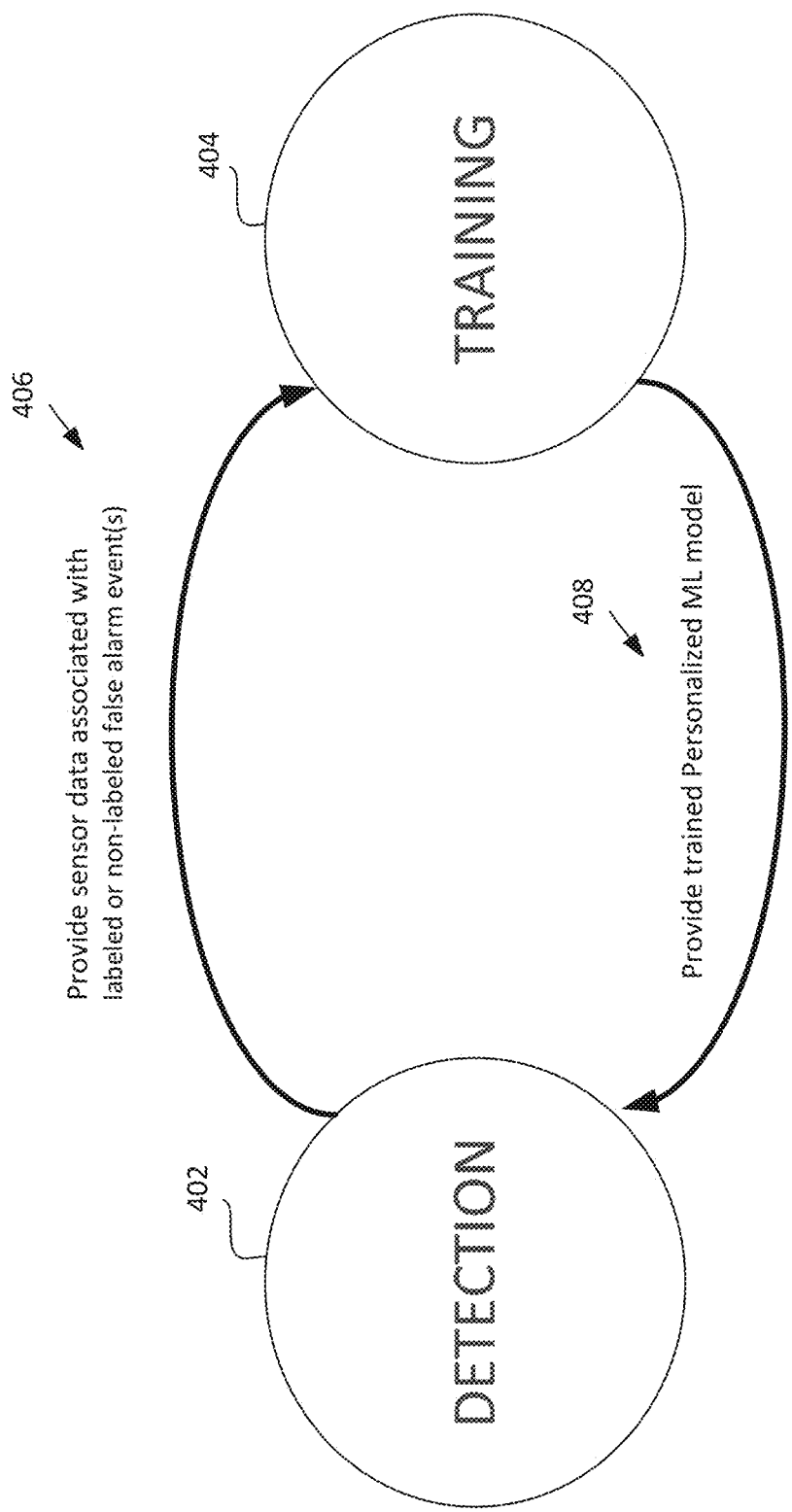
FIG. 4 illustrates the interdependencies between detection of fall events and training of a personalized Machine Learning (ML) model according to some embodiments.

According to some embodiments of the present disclosure, two of the fundamental features of the FS systems and methods are 1) the training of a personalized ML model of a user; and 2) detection of anomalous sensor data associated with anomalous events, which could be fall events or false alarm events, and the anomalous sensor data being used to detect true fall events and/or for use in training the personalized ML model of the user. Referring now to FIG. 4, which illustrates the close link and the interdependencies between the detection process 402 (i.e., inference) of fall events and the training process 404 of a personalized ML model. According to various embodiments, to detect (i.e., infer) a fall event, data collected from one or more sensors of a user (e.g., sensors of the user's mobile device) may be processed and fed into the personalized ML model of the user in order to detect an anomalous event. As will be further described herein, various approaches may be employed to determine whether the anomalous event is a fall event or a non-fall event. Note that once an anomalous event has been confirmed to be a fall event or a non-fall event, the associated sensor data may be associated with a labeled or non-labeled false alarm event(s).

If an anomalous event is determined to be a fall event, appropriate actions (e.g., issue alerts) can be taken. On the other hand, if the anomalous event is determined to be a false alarm event (e.g., a non-fall event, or at least the sensor data associated with the non-fall event, that is not recognized by the personalized ML model) or a fall event then at 406 the sensor data associated with labeled or non-labeled false alarm event(s) may be provided or fed to the personalized ML model to train (e.g., update) the personalized ML model. That is, in some cases, users may sometime label a false alarm event incorrectly. Once the personalized ML model has been trained at 404, the trained personalized ML model at 408 may be deployed in order to be used for fall detection. Although the training and detection processes are closely interdependent, in various embodiments, the two processes may be implemented at two different network nodes. For example, in some embodiments, the detection process may be implemented at a user's mobile device while the training process may be implemented on a cloud platform.

Turning now to FIGS. 1A, 1B, 1C, and 1D illustrating four network environments according to various embodiments. More particularly, FIGS. 1A, 1B, 1C, and 1D show how the detection process (which may generally be implemented by fall detection engine 16* of FIGS. 1A, 1B, 1C, and 1D) and the training process (which may generally be implemented by training system 14* of FIGS. 1A, 1B, 1C, and 1D) described above can be implemented at different network sites. Note that in the following, "*" represents a wildcard. Thus, references in the following description to, for example, "fall detection engine 16*" may be in reference to the fall detection engine 16a of FIG. 1A, the fall detection engine 16b of FIG. 1B, the fall detection engine 16c of FIG. 1C, or the fall detection engine 16d of FIG. 1D.

Referring particularly now to FIG. 1A, which illustrates an example network environment 100a according to some embodiments. More particularly, network environment 100a in some embodiments represents a cloud-based personalization (model management), training, and inference of normal activity with anomalies being considered possible falls. The network environment 100a includes a Fall Safety (FS) network system 10a, an end user device 20a that is associated with a user 22, a plurality of other users/devices 40, and network devices 50 that are all linked together via one or more networks 30. The FS network platform 10a may be implemented in a cloud platform and may comprise of one or more network devices such as one or more servers, data stores, and so forth. The end user device 20a may be a mobile device such as a smartphone or a wearable device (e.g., a smartwatch, a hearing aid, APPLE AIRPODS™, smartclothing, augmented reality (AR) device, etc.) that includes one or more sensors (e.g., accelerometer, gyroscope, GPS, barometer, heart rate monitor, and so forth) for monitoring activities and/or characteristics of the user 22, and/or other aspects related to the user 22 or the environment surrounding the user 22. The other users/devices 40 represents users/devices that are in communication with and employing the services of the FS network platform 10a. In various embodiments, the end user device 20a may collect various sensor data and transmit the collected sensor data to the FS network platform 10a. The sent sensor data may eventually be used for training a pre-trained ML model or a personalized ML model.

In some embodiments, the other users/devices 40 as well as user 22/end user device 20a may provide data including sensor data for developing and training generic ML models for different segments of the general population. It should be noted that user 22 and end user device 20a may essentially be viewed as one of the users/devices 40 of FIG. 1A. However, for illustrative purposes and for ease of explanation of various concepts the user 22 and end user device 20a have been separated out from the other users/devices 40.

The one or more networks 30 may include, for example, the Internet, intranets, extranets, wide area networks (WANs), local area networks (LANs), wired networks, wireless networks, or other suitable networks, or any combination of two or more such networks. The network devices 50 are associated with parties or entities who may be emergency contacts for users including, for example, 9-1-1 operators and services, doctors, hospitals, and so forth.

As illustrated, the FS network platform 10a may include a model management system 12, a training system 14a, and a fall detection engine 16a. In various embodiments, the model management system 12 may be configured to manage and maintain generic ML models for different segments of the general population as well as in some cases maintaining personalized ML models of different users. The training system 12a may be configured to train personalized, as well as generic in some cases, ML models. The fall detection engine 16a may be configured to detect (i.e., infer) a fall event related to user 22 using a combination of a personalized ML model (for detecting an anomalous event, which may or may not be a fall event) and other techniques for confirming occurrence of a fall event. Note that the detection 402 operation described above with respect to FIG. 4, as well as other operations for confirming detection of a fall event or non-fall event, may be performed by the fall detection engine 16a. Similarly, the training 404 operation described above with respect to FIG. 4 may be performed by the training system 114a.

Figure 1B:
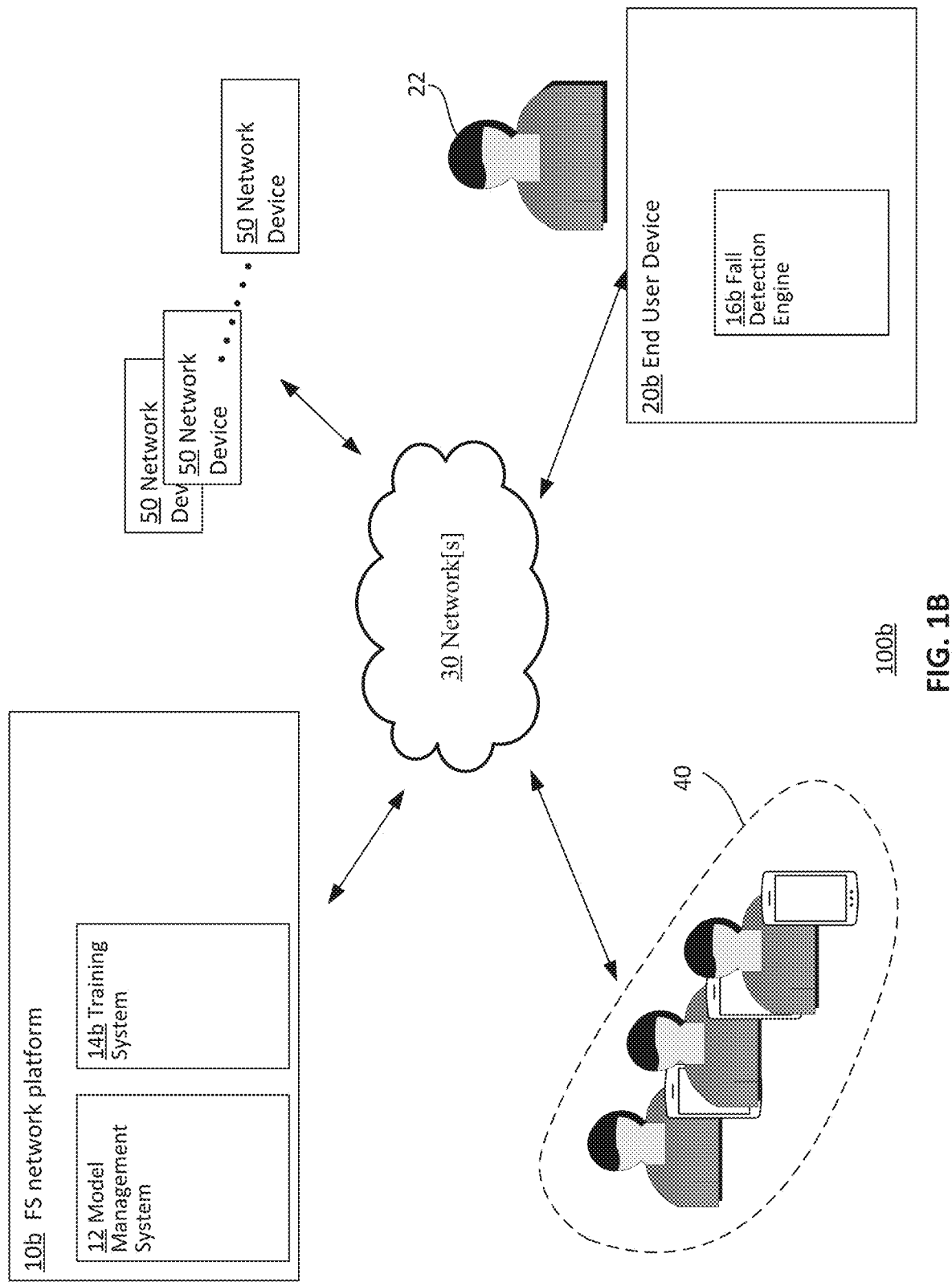
FIG. 1B illustrates another example network according to some embodiments.
Figure 1C:
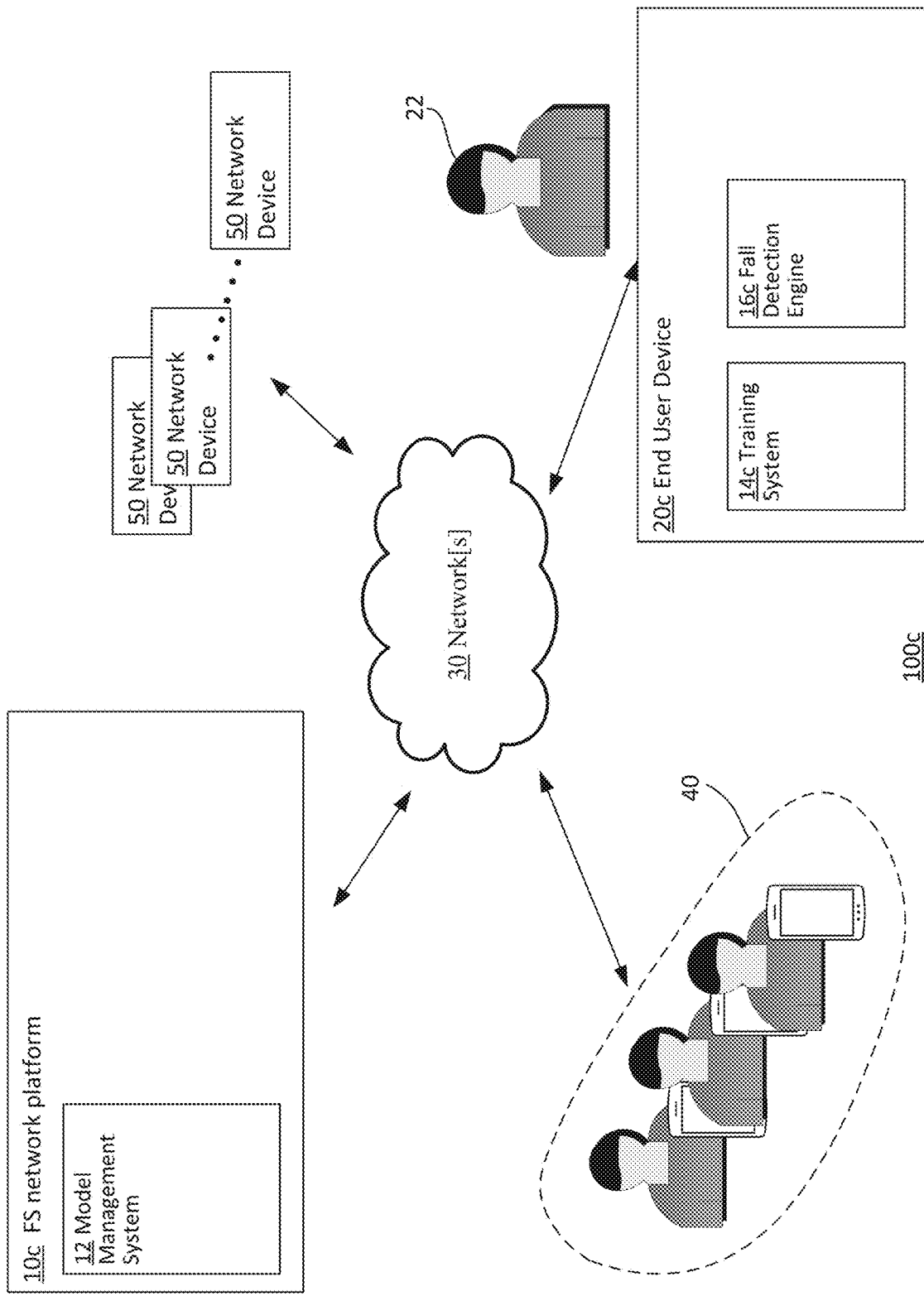
FIG. 1C illustrates another example network according to some embodiments.
Figure 1D:
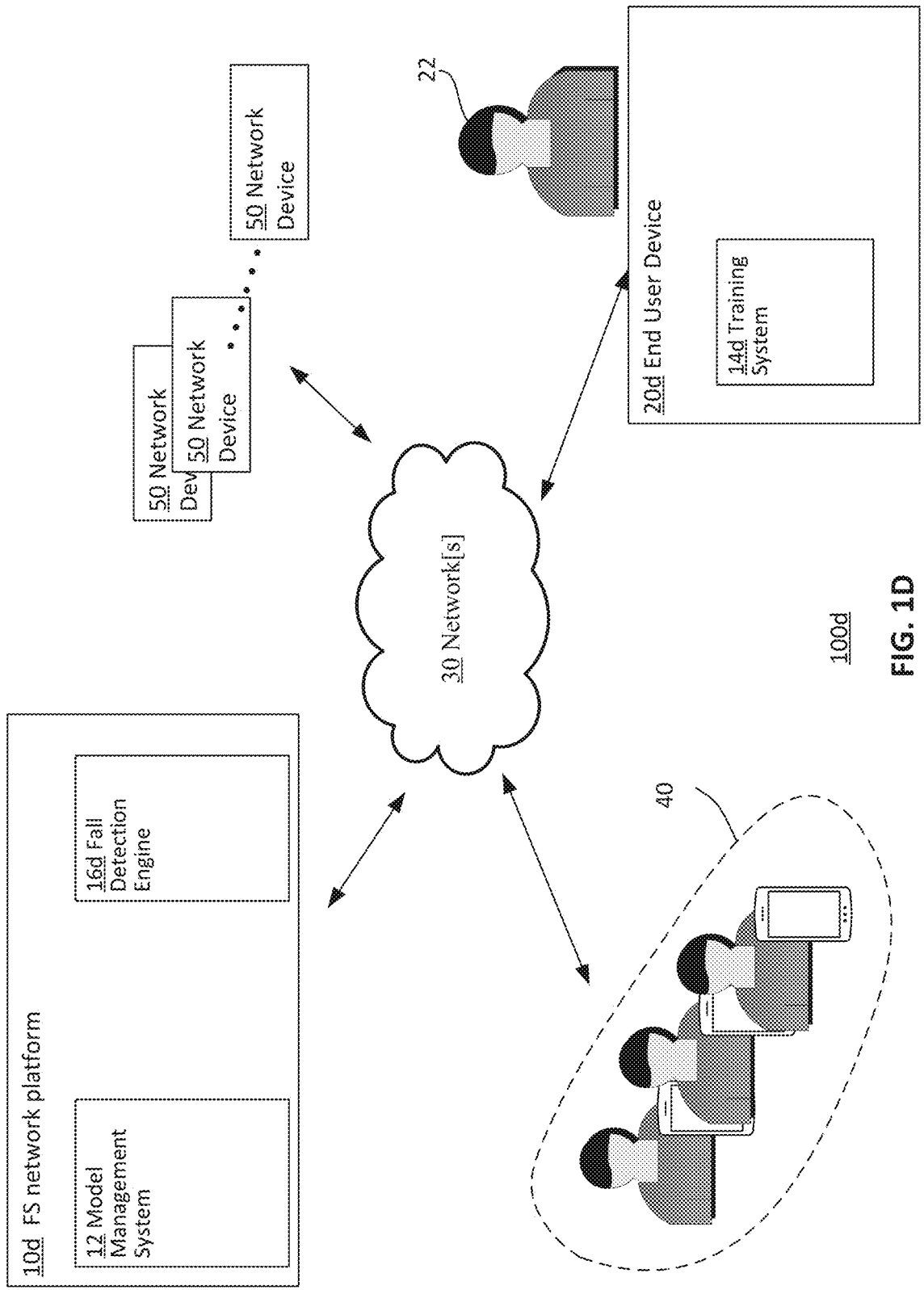
FIG. 1D illustrates another example network according to some embodiments.

Note further that in the embodiment illustrated in FIG. 1A both the training of a personalized ML model (as performed by training system 14a) and the detection of a fall event (as performed by the fall detection engine 16a), which may include detection of an anomalous event as well as confirmation that the anomalous event is either a fall event or a non-fall event, are implemented at the FS network platform 10a. As a result, the end user device 20a, with exception of transmission of sensor data to the FS network platform 10a (as well as some processing of the sensor data), plays a generally passive role in the embodiment illustrated in FIG. 1A. However, this will not always be the case as illustrated in FIGS. 1B, 1C, and 1D. That is, the only difference between the network environments 100a, 100b, 100c, and 100d illustrated in FIGS. 1B, 1C, and 1D is where the training system 14* and the fall detection engine 16* reside in their respective network environments 100*.

Note that references in the following to "FS systems" may be in reference to the model management system 12, the training service 14*, and/or the fall detection engine 16* as illustrated in FIGS. 1A, 1B, 1C, and 1D. As will be noted, these modular systems may be disposed at one or more network sites such as at the FS network platform 10* and/or at an end user device 20*. That is, references to the "FS systems" hereinafter are in reference to the various components/modules (e.g., the model management system 12, the training service 14*, and/or the fall detection engine 16*) that may be disposed at different network nodes and that are used to implement the various fall detection/ML model training operations to be described herein In contrast to the network environment 100a of FIG. 1A, the network environment 100b of FIG. 1B in some embodiments represents a cloud-based personalization (model management) and training, device based inference of normal activity with anomalies being considered possible falls. Meanwhile the network environment 100c of FIG. 1C in some embodiments represents a cloud-based personalization (model management), device based training and inference of normal activity with anomalies being considered possible falls. And finally, the network environment 100d of FIG. 1D in some embodiments represents a device-based personalization (model management), training, and inference of normal activity with anomalies being considered possible falls.

In the example network environment 100b of FIG. 1B, the fall detection engine 16b, which performs the same or similar operations as the fall detection engine 16a of FIG. 1A, is located at the end user device 20b. Thus, in the embodiment illustrated in FIG. 1B, the detection operation for detecting/confirming occurrence of a fall event is performed at the end user device 20b, while the training (e.g., updating) of the personalized ML model for user 22 is done at FS network 10b. As a result, whenever the FS network platform 10b finishes training the personalized ML model of user 22, the newly trained personalized ML model (e.g., a copy of the trained personalized ML model) may be sent/deployed to the end user device 20b for use by the fall detection engine 16b for detecting fall events as well as non-fall events. Once the fall detection engine 16b determines that an anomalous event is a non-fall event, the fall detection engine 16b may transmit to the training system 14b of FS network platform 10b the sensor data associated with the non-fall event for use by the training service 14b for training the personalized ML model of user 22 (e.g., training a copy of the personalized ML model of user 22 maintained by FS network platform 10b). In some embodiments, the sensor data transmitted to the training system 14b may be raw sensor data. In some embodiments, references to "raw sensor data" may be in reference to sensor data that have been minimally processed, for example, sensor data that only has been processed in order to be in a form that is transmittable over a wireless network and recoverable once reaching its destination. The FS network platform 10b (or the training system 14b) may then send at least a copy of the newly trained personalized ML model of user 22 back to the end user device 20b, replacing the old personalized ML model to detect future fall events.

In some cases, there may be certain advantages of locating the training system 14b at the FS network platform 10b and the fall detection engine 16b at the end user device 20b. For example, by locating the training system 14b, the battery life of the end user device 20b may be extended during training of a personalized ML model of user 22. That is, in some cases, the end user device 20b may be a small wearable device such as a pendant or a smartwatch with a small power pack (e.g., battery). For these situations, it may be desirable to have energy consuming operations, such as training of a personalized ML model, performed remotely. Meanwhile, locating the fall detection engine 16b at the end user device 20b may offer certain advantages. For example, by locating the fall detection engine 16b at the end user device 20b detection of fall events will not be interrupted when there are issues related to network connectivity.

FIG. 1C illustrates another example network environment 100c in which a training system 14c and a fall detection engine 16c are located at an end user device 20c. Note that the training system 14c and the fall detection engine 16c may perform essentially the same operations of the training systems 14a and 14b and the fall detection engines 16a and 16b of FIGS. 1A and 1B. Note also that the model management system 12, in the embodiments illustrated in FIGS. 1A, 1B, 1C, and 1D may supply a generic ML model to the training system 14* and/or the fall detection engine 16* of FIGS. 1A, 1B, 1C, and 1D for training the generic ML model to generate a personalized ML model for user 22 and/or for direct use in detecting fall events.

FIG. 1D illustrates yet another example network environment 100d in which a training system 14d is located at the end user device 20d and the fall detection engine 16d is located at the FS network platform 10d. Again, the training system 14d and the fall detection engine 16d of FIG. 1D generally perform the same functions of the training system 14a, 14b, and 14c and the fall detections engines 16a, 16b, and 16c of FIGS. 1, 2, and 3. In another implementation, but not illustrated here, both the FS network platform 10* and the end user device 20* may maintain copies of the training system 14* and the fail detection engine 16* for redundancy.

Figure 2:
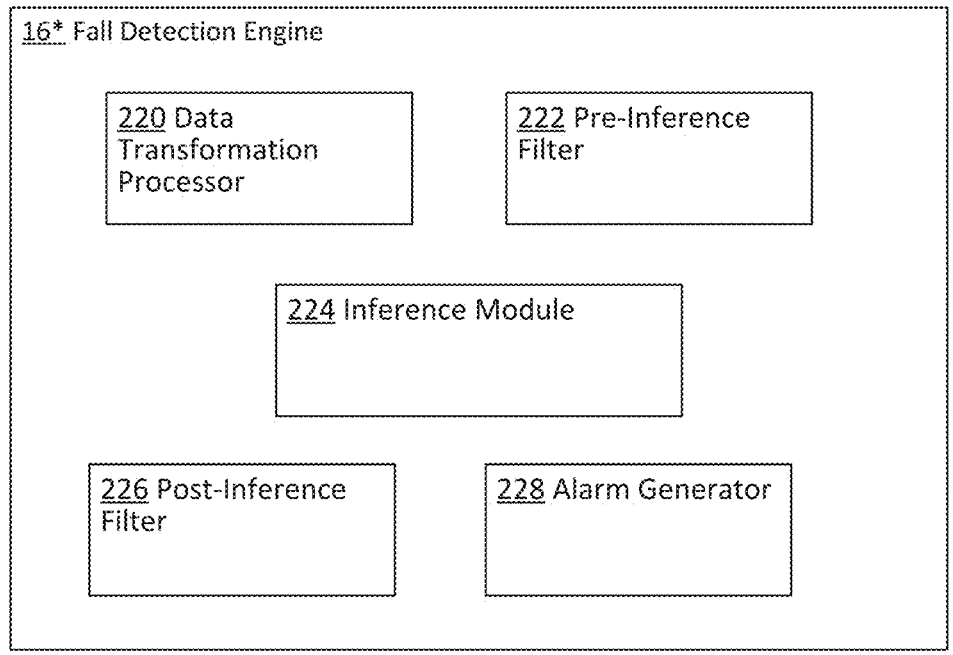
FIG. 2 illustrates components of an example fall detection engine according to some embodiments.

FIG. 2 illustrates the components of the fall detection engine 16* of FIGS. 1A, 1B, 1C, and 1D according to some embodiments. The fall detection engine 16* may include a data transformation processor 220, a pre-inference module 222, an inference module 224, a post-inference module 226, and an alarm generator 228. The various components may be used in combination to process sensor data, perform an initial filtering (pre-inferencing filtering) of the processed sensor data, infer a fall event by detecting an anomaly, perform a post-inference filtering to detect a fall event or a non-fall event (i.e., false alarm event), and to generate an alarm in response to detecting (inferring) a fall event. Although not illustrated here, in some embodiments, the inference module 224 may include one or more of the modules including, for example, the data transformation processor 220, the pre-inference filter 222, and/or the post-inference filter 226.

In various embodiments, the data transformation processor 220 may be designed to process (e.g., using advanced signal processing techniques) raw sensor data, which may be in the form of processed sensor data signal or signals, to produce processed sensor data that is usable by an ML model. The processing of the raw sensor data may include calculating feature values for windows of the raw sensor data. The data transformation processor 220 may also window the processed sensor data. For example, extracting processed sensor data that was collected within one-second of the occurrence of a suspect event (e.g., within a time window, which in this case is a little more than two-seconds—the time span of the suspect event plus one second for each side of the suspect event) and disregarding the other processed sensor data that were generated from raw sensor data collected before or after the time window (hereinafter simply "window"). Note that the ML learning windows may be any number of seconds including small windows from one to two seconds to 10 to 30 seconds or more. Also, using lookbacks (retaining state from previously processed windows) can help with accurate detection of anomalies.

The pre-inference filter 222 may be configured to receive from the data transformation processor 220 processed sensor data (e.g., processed sensor data signal or signals) and to filter out sensor data that are clearly not associated with fall events. For example, if the processed sensor data indicate no or very little movement by the user 22 (or by the end user device 20*) then the processed sensor data may be filtered out and the processed sensor data (and the user activities associated with it) may be disregarded. Alternatively, if the processed sensor data indicate that the user 22 fell towards earth that exceed a vertical distance threshold amount or vertical acceleration threshold amount, then that may be sufficient to flag the associated event as a fall event and may cause the alarm generator 228 to cause the end user device 20* to present (audibly or visually) a warning of a detected fall event with, in some cases, an option to cancel the alert, or alternatively cause the alarm generator 228 to transmit alert to one or more emergency contacts without giving the user 22 opportunity to cancel the alert (e.g., for cases when the detection of the fall event is with high confidence).

In some embodiments, inference module 224 may be configured to receive the processed sensor data that filters through the pre-inference filter 222 and to feed the processed sensor data to a personalized ML model to identify anomalous processed sensor data that are associated with an anomalous event, which could be a fall event or a non-fall event (i.e., false alarm event). In some alternative implementations, the inference module 224 may instead receive unprocessed sensor data and feed the unprocessed sensor data to a personalized ML model in order to identify anomalous sensor data that are associated with the anomalous event. The inference module 224 may comprise of one or more ML models. In some embodiments, the inference module 224 may comprise of multiple ML models that are strung together in an ensemble approach. For example, in one implementation the inference module 224 may include a generalized ML model and a personalized ML module that are bundled by chaining them together in code. In some cases, the inference module 224 may include the data transformation processor 220 and the pre-inference filter 222. In embodiments where the inference module 224 includes the data transformation processor 220 and the pre-inference filter 222, the inference module 224 may directly receive unprocessed and unfiltered sensor data. For these embodiments, the inference module 224 may take the unprocessed and unfiltered sensor data and process it and perform pre-inference filtering on the unprocessed sensor data. In various embodiments, processing of the sensor data (i.e., sensor data signal or signals) may include windowing the sensor data and calculating feature values for the windowed sensor data, which will be described in greater detail herein.

In some implementations, the inference module 224 may include a generalized ML model and a personalized ML model that are run by chaining them together inside a combined model filing using an ensemble approach. In another implementation, the inference module 224 may include a ML model that was formed by combining the generalized data and personalized data at training time. This may use a transfer learning technique to train faster. In yet another implementation, the inference module 224 may include more than two ML models, models that are run together to filter out false alarms (possibly one per false alarm). In some cases, the inference module 224 may include fall event ML model designed to detect falls including sensor data for detecting real falls. Note that although in some cases a personalized ML model may use one to two second windows, in other cases, it may use 10 to 30 second windows.

The post-inference filter 226 may be configured to additionally filter the processed sensor data (e.g., processed sensor data signal or signals identified by the inference module 224 as being anomalous processed sensor data) to determine whether the processed sensor data is in fact associated with a fall event or a non-fall event. For example, the post-inference filter 226 may be configured to determine whether processed sensor data that has been determined by the inference module 224 to be associated with an anomalous event, is in fact associated with a fall or non-fall event. To do so, the post-inference filter 226 may parse sensor data collected before or after the occurrence of the anomalous event in order to make that determination. Such data may indicate the movements of the user before or after the occurrence of the anomalous event that may indicate that the anomalous event is a fall or a non-fall event. For example, if sensor data collected after the anomalous event indicates or suggests that the user 22 was walking after the occurrence of the anomalous event, then it may be concluded that the anomalous event was in fact a non-fall event. On the other hand, if the user 22 is detected as laying on the ground and not moving for more than, for example, 15 seconds after the occurrence of the anomalous event, then it may be concluded that the anomalous event is in fact a fall event. Note that the phrase "sensor data" and the phrases "sensor data signal" or "sensor data signals" may be interchangeably used, and are therefore, synonymous unless indicated otherwise.

The alarm generator 228 may be configured to issue different levels of alarms or alerts in response to detection (or a strong inference) of a fall event in response to by the pre-inference filter 222, the inference module 224, and/or the post-inference filter 226 detecting (inferring) a fall event. For example, if the inference or detection of a fall event is with very high confidence (e.g., user 22 detected as falling vertically exceeding a threshold), the alarm generator 228 may transmit an alert to one or more emergency contacts (e.g., 9-1-1 system, private health monitoring service, doctors, caretakers, family and friend, and so forth) without giving the user 22 a chance to cancel the alert. If the detection or inference of a fall event is with moderate confidence (e.g., user 22 stumbles), then the user may be given a short time period to cancel the alert, and if no cancellation occurs within the time period, the alarm generator 228 issues alarms/alerts to one or more emergency contacts. For example, the user's mobile device may be prompted to display an alarm with an option to cancel within a short time period, for example, ten seconds. If the detection or inference of a fall is with low confidence (e.g., user 22 may have been a slipped) then the user's mobile device may be prompted to display an alarm with an option to confirm the alarm within a short time period. If the user 22 does not confirm a fall within the short time, the alarm is cancelled automatically and no alert is issued to emergency contact.

As will be recognized by a person of ordinary skill in the relevant art, the various modules and submodules (e.g., model management system 12, training system 14*, fall detection engine 16*, the data transformation processor 220, the pre-inference filter 222, the inference module 224 (including its ML models), the post-inference filter 226, and the alarm generator 228) illustrated in FIGS. 1A, 1B, 1C, 1D, and 2 may be implemented using a variety of techniques including using dedicated circuitry such as application specific integrated circuit (ASIC) and/or one or more processors executing software (e.g., computer-readable programming instructions that may be stored in one or more non-transitory storage media such as one or more CD disks, flash drives, hard drive, ROM, and so forth)

Figure 3A:
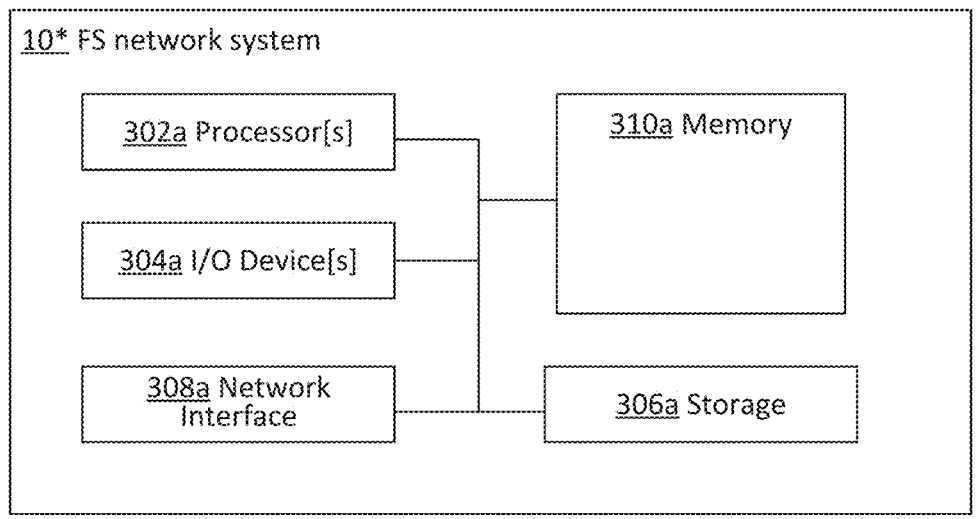
FIG. 3A is a block diagram of an example Fall Safety (FS) system.

FIG. 3A is a block diagram of the FS network platform 10* of FIGS. 1A, 1B, 1C, and 1D according to some embodiments. In various embodiments, the FS network platform 10* may comprise of a single network device such as a server, or may comprise of a plurality of network computer devices (servers) such as in a cloud platform. In some embodiments, the FS network platform 10* may get streaming data, in real time, from one or more sensors. As illustrated, the FS network platform 10* may include one or more processors 302a, one or more input/output (I/O) devices 304a, storage 306a, one or more network interfaces 308a, and memory 310a. The one or more processors 302a may include one or more microprocessors, CPUs, controllers, and so forth. The one or more I/O devices 304a may include one or more of a keyboard, a mouse, a microphone, a touchscreen, speakers, and so forth. The memory 310a may include both volatile (e.g., Random Access Memory or RAM, Dynamic RAM or DRAM, Static RAM or SRAM, and so forth) and non-volatile memory (e.g., read-only-memory or ROM, flash memory, and so forth). The storage 306a in some embodiments may supplement the memory 310a any may include, for example, magnetic storage disks, optical disks, tape memory, flash memory, and so forth. In various embodiments, the memory 310a and the storage 306a may be employed in order to store generic ML models, personalized ML model, and/or sensor data including raw sensor data related to fall and non-fall events. The one or more network interfaces 308a may include one or more network interface cards (NICs), computer ports, and so forth. In various embodiments, the memory 310a and the storage 306a may store computer or machine-readable programming instructions for implementing at least some of the modules and sub-modules illustrated in FIGS. 1A, 1B, 1C, 1D, and 2 as well as for executing at least some of the operations to be described herein. In some embodiments, the memory 310a and the storage 306a may store generic ML models, personalized ML models, and/or sensor data.

Figure 3B:
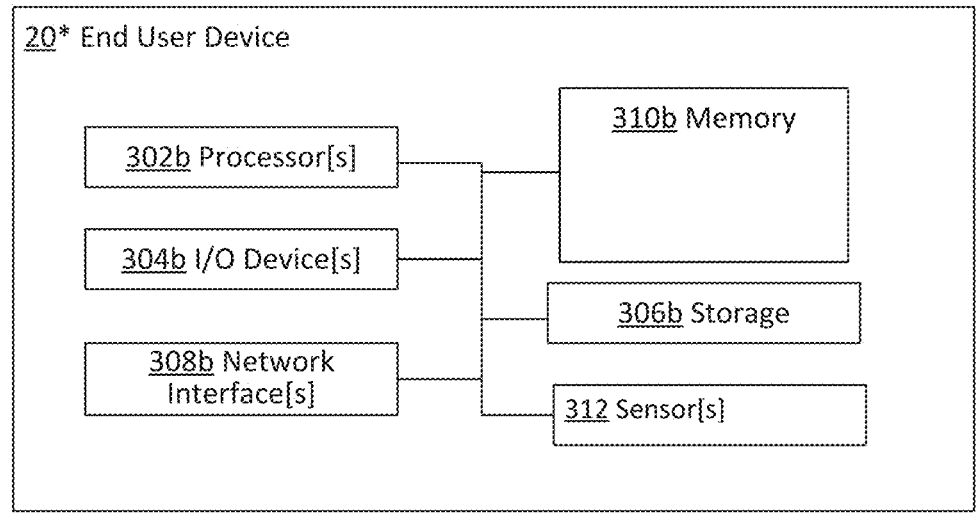
FIG. 3B is a block diagram of an example end user device.

FIG. 3B is a block diagram of the end user device 20* of FIGS. 1A, 1B, 1C, and 1D according to various embodiments. As previously described, in various embodiments, the end user device 20* may have any one of a variety of form factors including, for example, a smartphone or a wearable device (e.g., smartwatch, augmented realty device, pendant, APPLE's AIRPOD and so forth). The end user device 20* may include the same type of components included in the FS network platform 10* including, for example, one or more processors 302b, one or more I/O devices 304b, storage 306b, one or more network interfaces 308b, and memory 310b. These components may perform the same or similar functions as their counterparts included in the FS network platform 10* of FIG. 3A. In addition, the end user device 10* may include one or more sensors 312 including, for example, an accelerometer, a gyroscope, GPS, a barometer, microphone, compass, camera, heart rate monitor, and so forth. Note that the memory 310b and the storage 306b may store computer or machine-readable programming instructions for implementing at least some of the modules and sub-modules illustrated in FIGS. 1A,1B, 1C, 1D, and 2 as well as for executing at least some of the operations to be described herein.

Figure 5:
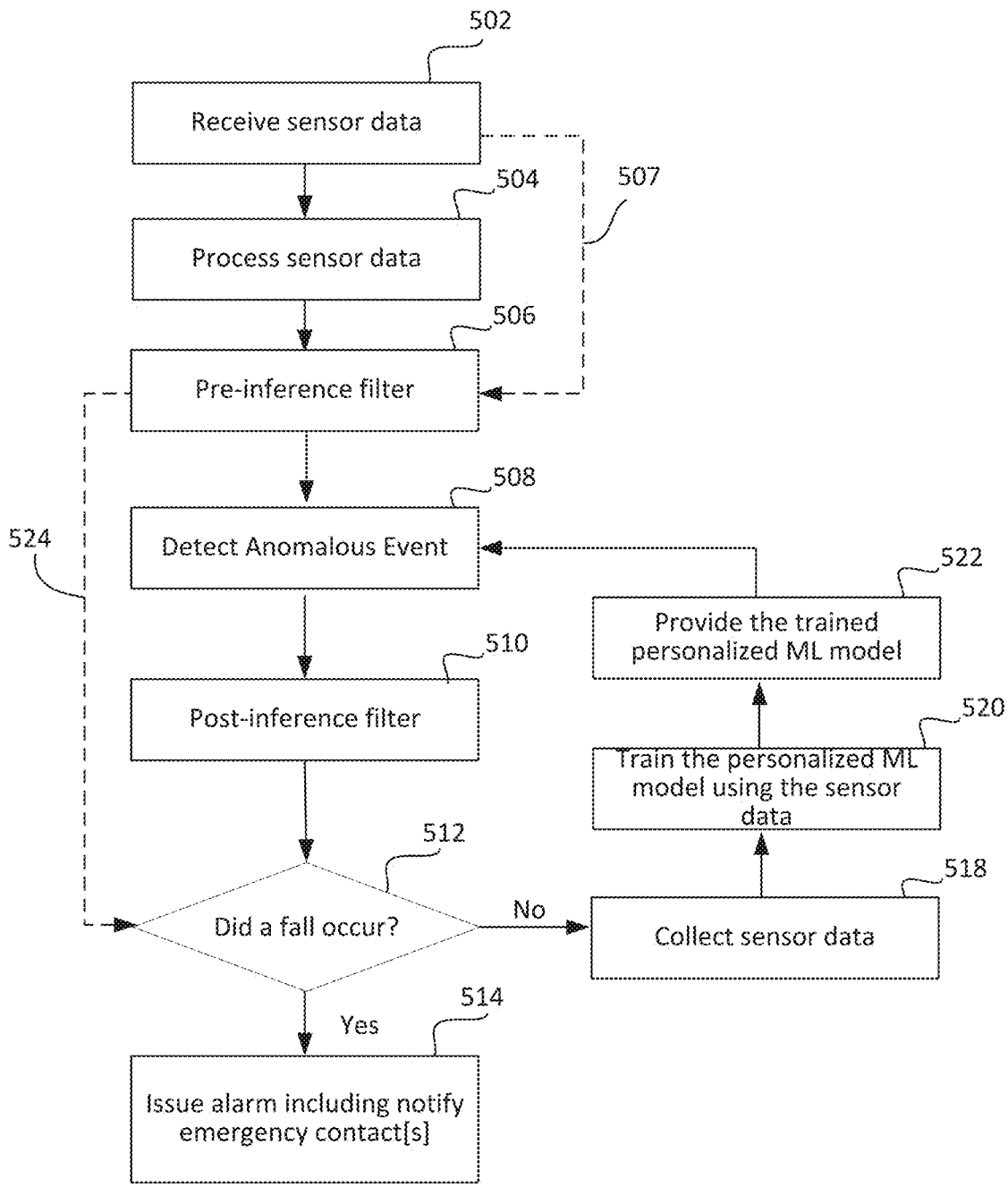
FIG. 5 is an example high-level process for detecting a fall event and training a personalized ML model according to various embodiments.

Referring to FIG. 5, which is an example high-level flow diagram showing an illustrative process 500 for detecting a fall event and training a personalized ML model according to various embodiments. In some embodiments the detection or inference of a fall event, which generally corresponds to operations 502 to 514 of FIG. 5 may be implemented by the fall detection engine 16* of FIGS. 1A, 1B, 1C, 1D, and 2 while the training of a personalized ML model, which generally corresponds to operations 518 to 522, may be implemented by the training system 14* of FIGS. 1A, 1B, 1C, and 1D. To facilitate understanding of process 500, the following description of process 500 will be provided with references to the user 22, end user device 20*, the FS network platform 10*, and other aspects of FIGS. 1A, 1B, 1C, and 1D.

In some embodiments, process 500 may begin at 502 when sensor data (e.g., sensor data signals) associated with a user 22 is received by, for example, a fall detection engine 16* from end user device 20*. In embodiments where the fall detection engine 16* is located at the FS network platform 10* the sensor data may be received via one or more networks 30. In embodiments where the fall detection engine 16* is located at the end user device 20*, the sensor data may be obtained directly from the one or more sensors 312 of the end user device 20*. The received sensor data, which may be in the form of raw sensor data, may be obtained from a variety of sensors including, for example, accelerometer, gyroscope, heart rate monitor, compass, barometer, camera, microphone, and so forth. In some embodiments, the sensor data may be continuously or semi-continuously received for at least an extended period.

At 504 the received sensor data (i.e., sensor data signals) is processed using, for example, advanced signal processing techniques. The processed sensor data may be windowed to extract only relevant data. For example, although sensor data may be continuously collected for an extended period, the processed sensor data may only be fed in some cases to the personalized ML model in overlapping blocks (e.g., windows). In some embodiments, the sensor data may be processed by calculating feature values for sensor data window.

At 506, pre-inference filtering of the windowed processed sensor data may be performed. This may involve at least filtering out processed sensor data that are clearly not associated with fall events. For example, if the processed sensor data indicates no or very little movement by the user 22 (or by the end user device 20*) then it may be concluded, with relatively high confidence, that there is no fall event associated with the processed sensor data and that the processed sensor data (and the user activities associated with it) may be disregarded. Alternatively, if the processed sensor data indicate that the user 22 fell towards earth that exceed a threshold vertical distance or threshold acceleration, then that may be sufficient to permit the associated processed sensor data to be fed, for example, to the personalized ML model for anomaly detection.

In cases where it is determined that the processed sensor data indicates with high confidence that it is associated with a fall event or determines that the processed sensor data indicates with high confidence that it is associated with a non-fall event, then process 500 moves directly to 512 as illustrated by 524. Note that in some embodiments, the process operation 504 and the pre-inference filtering operation 506 may be implemented by the data transformation processor 220 and the pre-inference filter 222, respectively. Alternatively, these operations may be performed by the inference module 224 (e.g., when the inference module 224 includes the data transformation processor 220 and the pre-inference filter 222). In some embodiments, and as illustrated by 507. the sensor data processing 504 may be skipped and the pre-inference filtering 506 may be performed after the reception of the sensor data at 502. That is, as one of ordinary skill in the art will recognize, such filtering may be performed either on processed sensor data or on "raw" sensor data. For example, if the sensor data includes motion sensor data associated with the user 22, then there would be no need to do advanced signal processing on the sensor data if the raw sensor data clearly shows that the user 22 was inactive and moving very little (e.g., sleeping).

At 508 the processed sensor data that was not filtered out by the pre-inference filtering at 506 may be fed to a personalized ML model associated with the user 22 to detect an anomaly (e.g., to detect an anomalous processed sensor data signal or signals that has a pattern that is not recognized by the personalized ML model). At 508, the inference module 224 may ascertain the anomalous event associated with the anomalous processed sensor including, in some cases, ascertaining the raw sensor data associated with the anomalous event. The anomalous event may either be an actual fall event or a non-fall event that is not currently recognized by the personalized ML model as being a non-fall event (note that if the processed sensor data associated with the anomalous event had been recognized by the personalized ML model then it would not be an anomaly).

At 510 the anomalous processed sensor data outputted by 508 may be filtered in a post-inference filtering. In some embodiments, the post-inference filtering may be performed by the post-inference filter 226 to determine whether the anomalous processed sensor data in fact is associated with a fall event or with a non-fall event. To do so, the post-inference filter 226 may parse sensor data collected before or after the occurrence of the anomalous event associated with the anomalous processed sensor data in order to make that determination. For example, if sensor data collected after the anomalous event indicates or suggests that the user 22 was walking after the occurrence of the anomalous event, then it may be concluded that the anomalous event was in fact a non-fall event. On the other hand, if the user 22 is detected as laying on the ground and not moving for more than, for example, 15 seconds after the occurrence of the anomalous event, then it may be concluded that the anomalous event is in fact a fall event.

At 512 a determination is made as to whether the detected anomalous event is a fall event. There are a number of ways that this can be achieved. In some embodiments, the user (who is the one being monitored) may be prompted to indicate whether the anomalous event was a fall event or a non-fall event. In some cases, if the user does not respond, it may be presumed that a fall event had occurred and that the user is incapacitated. In some embodiments, the determination may be based on the results of the post-inference filtering. In some cases, the determination made at 512 that a fall event had occurred will be based on the determination made at 506 that a fall event had occurred with high confidence.

At 512 if a fall event is determined or inferred to have occurred (in some cases, it may not be possible to definitively determine that a fall event did occur) then an alarm or alert is issued including notifying emergency contacts (e.g., 9-1-1 service, private medical services, caretaker, friends and/or families, and so forth) at 514. Note that in some cases when the pre-inference filter 506 or the post-inference filter 512 determines that a fall has occurred with high confidence, then process 500 may move directly to operation 514

If, on the other hand, it is determined at 512 that a non-fall event had occurred then at 518 raw or processed sensor data associated with the anomalous event including, in some cases, data collected immediately prior to or immediately following the occurrence of the non-fall event may be collected by, for example, the training system 14*. For example, in the implementation illustrated in FIG. 1B where the training system 14b is located at the FS network platform 10b, the FS network platform 10b may collect the sensor data from the end user device 20b via one or more networks 30. The sensor data collected may be data collected from a variety of sensors including, for example, motion sensors (e.g., accelerometer, gyroscope, etc.) as well as in some cases other types of sensors (e.g., GPS, barometer, heart rate sensor, etc.).

At 520 the personalized ML model that was used previously to detect the anomaly is trained using at least a portion of the sensor data collected to generate a newly trained personalized ML model for the user 22. In some embodiments, the training of a personalized ML model may involve processing raw sensor data (e.g., the collected sensor data in some cases may be raw sensor data) to produce processed sensor data that is in a form usable by the personalized ML model, and continuously or repeatedly feeding the processed sensor data to the personalized ML model until it is fully trained so that it is able to recognize the unique pattern of the processed sensor data signals. In some embodiments, the sensor data used to train the personalized ML model may be raw unprocessed sensor data. Note that in various embodiments the sensor data used to train the personalized ML model may merely be a copy of the sensor data that was processed (or not processed) and identified as being associated with a non-fall event.

The trained personalized ML model may then be provided at 522 to, for example, the fall detection engine 16* for detecting anomalies, resulting in process 500 returning to operation 508 where additional anomalous event or events may be detected. As illustrated, the process of detecting anomalies, determining whether a fall event or non-fall event has occurred, and training and updating the personalized ML model may be repeated in a looping fashion so that as the training system 14* collects more data points, a more accurate personalized ML model is produced.

Figure 6A:
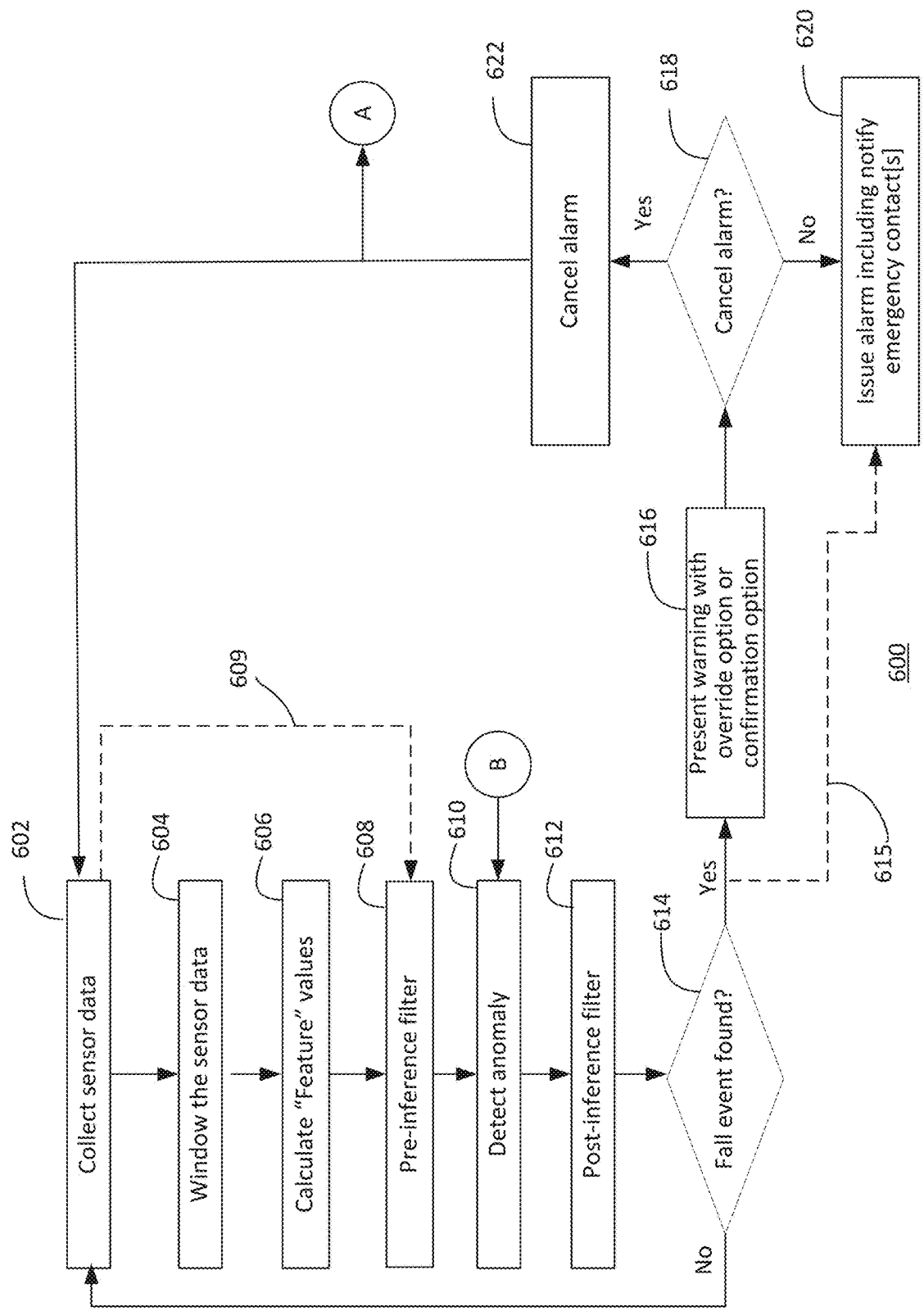
FIGS. 6A and 6B illustrates an example process for detecting a fall event and training a personalized ML model according to various embodiments.
Figure 6B:
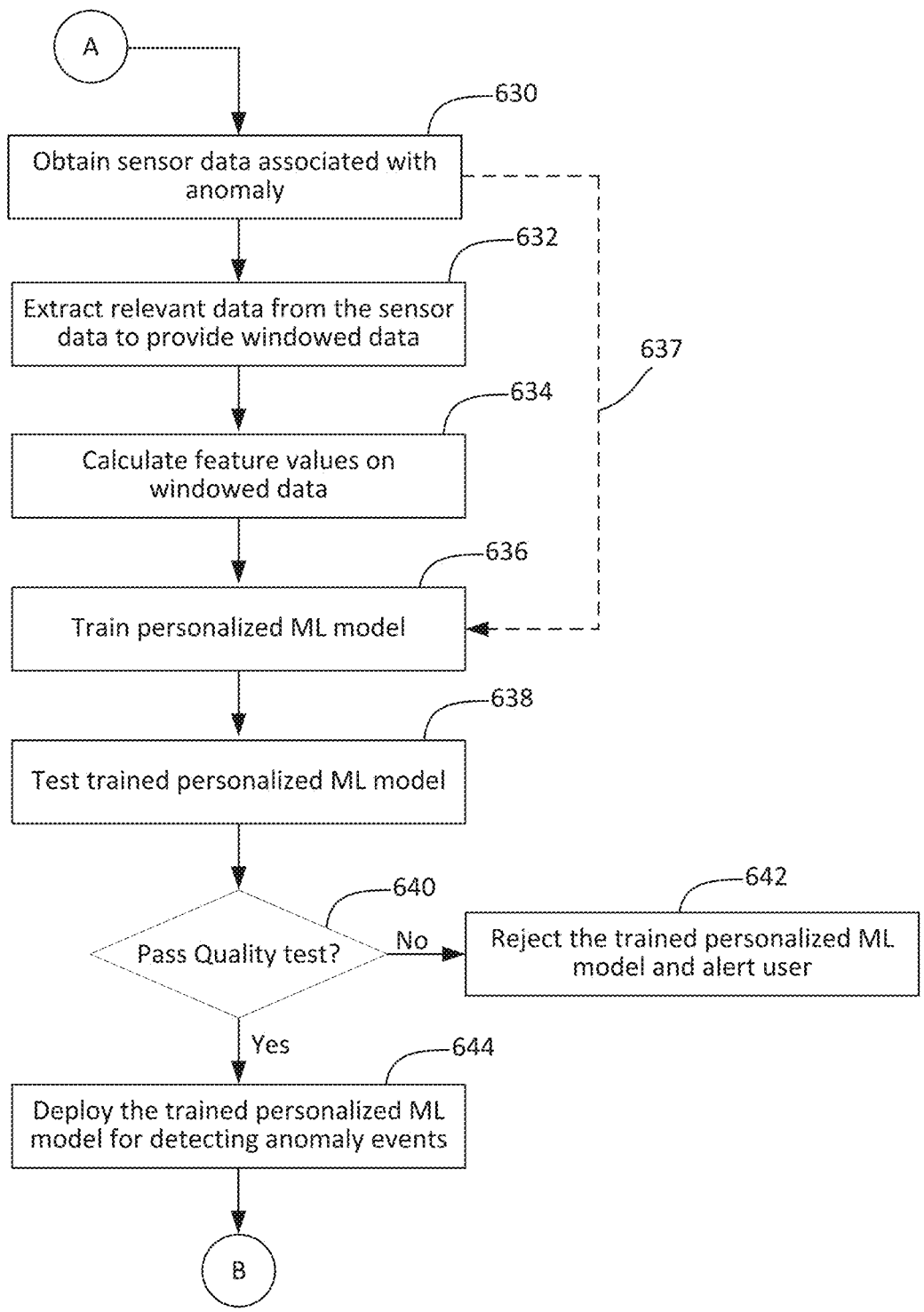

Turning now to FIGS. 6A and 6B illustrating an example flow diagram showing an illustrative process 600 for detecting or inferring a fall event and training a personalized ML model according to various embodiments. In some embodiments, process 600 may be viewed as a more detailed version of process 500 of FIG. 5. As in process 500, certain operations (e.g. operations 602 to 622) may be executed by the fall detection engine 16* of FIGS. 1A, 1B, 1C, 1D, and 2, while other operations (e.g., 630 to 644) may be executed by the training system 14* of FIGS. 1A, 1B, 1C, and 1D. To facilitate understanding of process 600, the following description of process 600 will be provided with references to the user 22, end user device 20*, the FS network platform 10* of FIGS. 1A, 1B, 1C, and 1D.

In some embodiments, process 600 may begin at 602 when sensor data is collected by, for example, the fall detection engine 16*. At 604 the collected sensor data, which may be raw sensor data, may be windowed.

In some embodiments in order to place the raw sensor data into a form that is usable by the personalized ML model, the windowed sensor data may be subjected to advanced signal processing to calculate "feature" values for the windowed raw sensor data at 606. Feature values are what the personalized ML model may use to detect or identify anomaly sensor data (e.g., anomaly sensor data signals), and by implication, anomalous events associated with that anomaly senor data. For example, many Artificial Intelligence (Machine Learning) algorithms attempt to classify data into groups. A well-known example is GOOGLE's image classifier (a Deep Convolutional Neural Network) for GOOGLE PHOTOS.

By taking labeled images of different objects (e.g. pictures of cats & dogs from GOOGLE's search engine) & sending the raw pixels into this classifier, it is able to reliably learn the difference between a cat, a dog, a rabbit, a tree, etc. That is, certain features of, for example, cats will cause the raw pixels of pictures of cats to have distinct "features." For example, the pointed ears of cats, the shape of cat eyes and nose will cause certain pixels of cat pictures to be distinct (e.g., distinct features). In turn, the AI may look for these features or feature values to identify cat pictures. Similarly, feature values from the windowed sensor data may be calculated to provide useful data that the personalized ML model can understand. The result of 606 is a windowed processed sensor data (i.e., windowed processed sensor data signal or signals)

At 608 the windowed processed sensor data may be pre-inference filtered similar or the same as the pre-inference filter operation of 506. This may involve at least filtering out windowed processed sensor data that are clearly not associated with fall events. In some embodiments, the pre-inference filtering operation of 608 may be performed on raw sensor data right after the sensor data was collected at 602 and skipping 604 and 606 as illustrated by 609. That is, the pre-inference filtering 608 can be performed using raw sensor data or using processed sensor data (e.g., sensor data that has been windowed and feature values calculated). The sensor data that survives the pre-inference filtering 608 may then be fed to a personalized ML model to detect anomalies (e.g., anomalous sensor data) at 610, which may be associated with fall events or non-fall events.

At 610 the windowed processed sensor data that has been filtered and that provides feature values or raw sensor data may be fed to the personalized ML model, which in some embodiments may be an anomaly detection neural network (ADNN) to detect anomaly processed sensor data (as well as the anomalous event or events associated with the anomaly sensor data). Upon being fed the processed sensor data (or raw sensor data), the personalized ML model may look for anomalies (e.g., those processed sensor data signals or raw sensor data having a pattern that is not recognized by the personalized ML model as being associated with non-fall events or even being associated with known fall events). In some embodiments, feature values may be calculated for two-second windows of acceleration data (or other types of movement data). Note that Machine Learning windows may be any number of seconds including small windows from one to two seconds to 10 to 30 seconds or more. Using lookbacks (retaining state from previously processed windows) can help with accurate detection.

At 612, the personalized ML model filter out or disregards windowed processed sensor data that have been determined to be anomalies but are deemed not associated with a fall event similar or same as operation 510 of FIG. 5. For example, sensor data collected after the anomalous event may be parsed to determine if the user is detected as walking around after the anomalous event associated with the anomaly processed sensor data, then that may be a strong inference that no fall event has occurred. Other factors may also be used in order to filter out "false positives" including checking the heart rate of the user after the anomalous or suspect event, checking user's location, and so forth.

At 614 a determination is made as to whether a fall event has, in fact, occurred with respect to the detected anomaly. Again, this may be accomplished by looking at various sensor data that may not have been considered when identifying an anomaly. Also, in some cases if the calculated feature values exceed certain threshold values, that may be conclusive or strong inference that the associated anomalous event was, in fact, a fall event. Of course, the flip side of that is that if the calculated feature values are below a certain minimum threshold value, then that may indicate that the anomalous event is a non-fall event. The determination at 614 may also include determining confidence levels of fall detection such as high, medium, and low confidence levels.

If a fall event is not found or detected, the process 600 returns to 602. If a fall event is found (e.g., the fall detection engine concludes or strongly infers that a fall has occurred) then at 616 the end user device 20* is prompted to present (e.g., display) a fall detection warning with override option for the user 22 to see or hear. Various levels of warning/alerts may be provided depending upon the type of fall event has been detected (e.g., a fall, a stumble, or a slip). For example, if a fall is detected with low confidence, then the end user device 20* may be prompted to display a warning of a detected fall and if the user does not confirm the fall within a certain period of time, such as within 30 seconds, then the fall alarm is canceled and no further actions may be taken. On the other hand, if a fall was detected with medium confidence then the end user device 20* may be prompted to display a warning of a detected fall and an option to cancel the alarm within a certain time period (e.g., 30 seconds). If the user 22 does not respond within the allotted time, an alert is sent out automatically to one or more emergency contacts. Note that if a determination was made that a fall event had occurred with high confidence at 614, then process 600 may move directly to 620 skipping 616 and 618 as illustrated by 615, and an alert is sent out to one or more emergency contacts without giving the user 22 a chance to confirm or cancel the alarm and the process 600 moves directly to 620.

If a fall event was detected with medium level of confidence, then at 616 the end user device 20* may be prompted to present (visually or audibly) a warning of fall event detection and an option to cancel the alarm. On the other hand, if a fall event was detected with low confidence, then a warning of a fall event detection may be prompted to be presented by the end user device 20* with an option to confirm the fall event, and if no confirmation is made within a certain period of time, the alarm is canceled and no further action may be taken. Note that in some alternative embodiments, whenever a fall event is detected, and regardless of level of confidence, the end user device 20* may be prompted to present a warning of the detected fall event with an option to cancel the alarm.

At 618 a determination is made to cancel or not cancel the alarm depending upon whether the user 22 confirms the fall, does not response to a warning within a certain time period, or opts to override the alarm as described above. If the alarm is not cancelled then at 620 an alarm or alert is issued to one or more contacts. On the other hand, if it is determined that the alarm is be canceled then at 622 the alarm is canceled and process 600 returns to 602.

Note also that if, for example the user 22 cancels the alarm (either by overriding the alarm or not taking any action to confirm the fall event) then the sensor data associated with the false alarm may be used to train the personalized ML model as will be illustrated in FIG. 6B. Referring now to FIG. 6B, after the alarm is canceled at 620, raw sensor data that was determined to be associated with an anomalous non-fall event (e.g., an anomalous event that was determined to be an unrecognized fall event) may, at 630, be obtained by the training system 14* for use in training the personalized ML model.

Although not illustrated, in some embodiments, the obtained sensor data, which may be raw sensor data, may be saved to the cloud (e.g., FS network platform 10*). At 632 relevant data may be extracted from the raw sensor data to provide windowed data. For example, data collected well before or well after the occurrence of the non-fall event may be discarded. At 634, feature values of the windowed sensor data may be calculated. In some embodiments, the feature values may be calculated by applying formulas over each window.

At 636, the personalized ML model of the user 22 is trained using the calculated feature values. In some embodiments, in order to train the personalized ML model, the personalized ML model may be continuously or repeatedly fed the feature values. In some embodiments, the copies of the calculated feature values, with slight variations may be repeatedly used to train the personalized ML model. Such training may help the personalized ML model recognize a non-fall event each time it occurs and even if the non-fall event occurs in slightly different ways. For example, if the non-fall event is the user 22 riding a short horse, the collected sensor data for that activity may be copied with slight variations so that the personalized ML model will recognize the user riding a tall horse. In some alternative embodiments, the operation for extracting relevant data at 632 and the operation for calculating feature values may be omitted. Instead, process 600 may move directly from the operation for obtaining sensor data at 630 to the operation for training the personalized ML model at 636. In other words, in some embodiments, the training of the personalized ML model at 636 may only require the use of raw sensor data (e.g., non-processed non-windowed sensor data).

To determine whether the personalized ML model has been adequately trained, the personalized ML model is quality tested at 638. The quality test is done to make sure, for example, that falsely labeled sensor data does not cause the personalized ML model to not recognize true fall events. That is, some users will, for one reason or another, tend to label true fall events as non-fall events. By doing so, true fall events may be trained out of the personalized ML model. In order to ensure that the personalized ML model is accurately detecting true fall events, sensor data associated with true fall events may be fed to the personalized ML model in order to see if the personalized ML model recognizes that the sensor data is associated with a fall event.

At 640 a determination may be made to determine whether the trained personalized ML model has passed quality test. If the trained personalized ML model does not pass the test, then the trained personalized ML model is rejected and the user 22 is alerted at 642. If, on the hand, the trained personalized ML model does pass the test, then the trained personalized ML model is deployed (e.g., deployed to the fall detection engine 16*) for use in detecting anomaly/fall events at 644. In order to present the trained personalized ML model to the fall detection engine 16*, in some embodiments, the trained personalized ML model may be transmitted to the fall detection engine 16* via one or more networks 30 from the training system 14* (see the embodiment illustrated in FIG. 1B where the training system 14b is located at the FS network platform 10b and the fall detection engine 16b is located at end user device 20b)

Note that although the above processes are designed to train personalized ML models, these procedures could also be used to train generic ML models for specific demographic groups. For example, in the above example, the sensor data that was associated with non-fall events that are used to train the personalized ML model of user 22 may also be passed on to the model management system 12 in FIGS. 1A, 1B, 1C, and 1D to help train the generic ML model associated with user 22. It should be noted, however, that in some embodiments, the reporting of sensor data associated with a single incidence of a non-fall event of an individual may not actually cause the relevant generic model to be modified. That is, for generic ML models, the more such incidences are reported, the more likely that the generic ML model will be modified or trained to recognize that such non-fall events are common to the entire population group associated with the generic ML model.

For example, if the user 22 goes horseback riding, and the sensors of the end user device 22 detects unusual movements that the fall detection engine 16* does not initially recognize but eventually determines that it is related to a non-fall event, then that sensor data may be used to train the personalized ML model of the user 22. That sensor data may also be provided to the model management system 12 to hopefully train the generic model to recognize such data as related to a non-fall event. In some cases, a single reported case of sensor data related to horseback riding may not cause the generic ML model to be trained to recognize such sensor data. However, if more members of the same demographic group participate in horseback activities, and as a result, the same type of non-fall movements are being reported, then that may cause the generic model to be trained to recognize such sensor data as being associated with non-fall activities.

Note that although the operations depicted in process 500 and process 600 of FIGS. 5 and 6A and 6B appear to be executed in a specific order, one of ordinary skill in the relevant art will recognize that many of the operations may be executed in an order that is different from how they are illustrated in processes 500 and 600. For example, in FIG. 6A, operations 604 and 606 may be executed in reverse order than the order that is depicted in FIG. 6A (e.g., operation 606 occurring before 604)

In some embodiments, the fall detection engine 16* may determine or infer whether the end user device 2 has fallen by determining whether the end user device 20* that is being held or being worn by the user 22 has fallen towards earth at specific velocity/acceleration, or distance that exceed certain thresholds. To do so, the appropriate coordinate system may need to be used in accordance with various embodiments. That is, most mobile devices have default coordinate systems. However, to accurately determine how fast and far a mobile is falling towards earth, a combination of the device default coordinate system and earth's coordinate system may be used.

In some embodiments, using an accelerometer of a mobile device, the device's accelerations (X, Y, and Z axes) at 100 Hz (a sample every 0.01s) 24 hours a day in the background may be captured. Each value may be returned as a real number from "−16 to 16," where the unit is in "Gs," where a G is 9.8 m/s$^2$ (acceleration from gravity). Using a gyroscope, the orientation of the device may be detected based on the rotational position of the sensors (and the device) relative to the earth. Using the detected orientation, the effect of earth's gravity pull may be subtracted out to get the user's true acceleration. This may also show which way is down, which is important for detecting falls toward the ground. Now that the user's true acceleration towards the ground is known, this value/equation can be integrated twice to calculate the vertical displacement (i.e. relative position). That is, by doing so, a determination may be made as to how far the person fell.

Post-fall, orientation+motion may also be used to help the personalized ML model to distinguish between putting the mobile device on a table verses being in someone's pocket and lying on the ground (e.g. person tends to be less horizontal, person tends to breathe and/or shake if he or she has a seizure). Heart rate on the mobile device (e.g., smartwatch) may also indicate that a human body is adjacent to the mobile computing device 702 and if the heart rate is abnormal.

Figure 7:
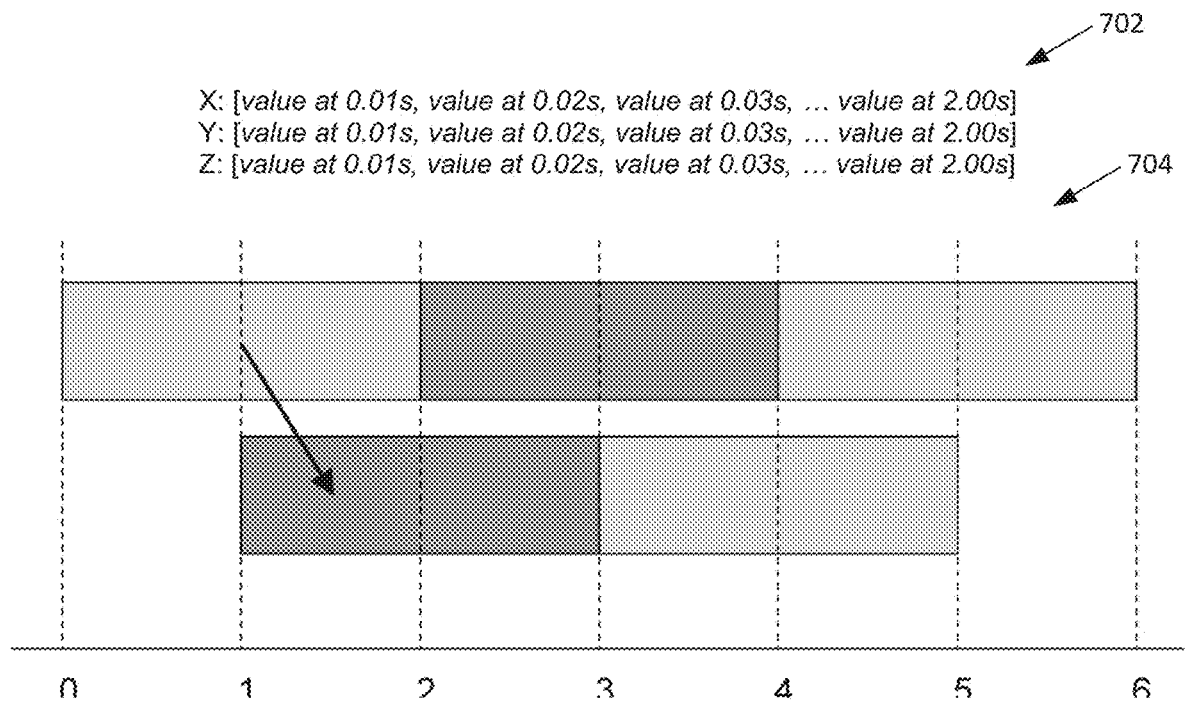
FIG. 7 illustrates an example rolling window processing.

As discussed above, in order to detect anomalies using a personalized ML models, the windowed sensor data must first be processed in order to calculate feature values for the windowed data. That is, although motion data including acceleration data are continuously captured by the FS systems (e.g., the fall detection engine 16* and the training system 14*), such data may not be directly fed to the personalized ML model. Instead, time windowing and feature calculations may be performed on such data, and the feature values may be fed into the personalized ML model. For example, the fall detection engine 16* may first window the data. The fall detection engine 16* may use a simple two-second "rectangular window" with one-second of overlap. Given the 100 Hz sampling rate and 3 axes, that results in a 3×200 matrix of values per window—see ref. 702 in FIG. 7, which also illustrates an example rolling window processing 704 (depicting one-second overlapped windows). In various embodiments, the personalized ML model is an Anomaly Detection Neural Network or ADNN. In alternative embodiments, other types of neural networks and machine learning model types (e.g. LSTM (Long Short-Term Memory) network, multiple linear regression model, or random forest classifier) may be employed.

Figure 8A:
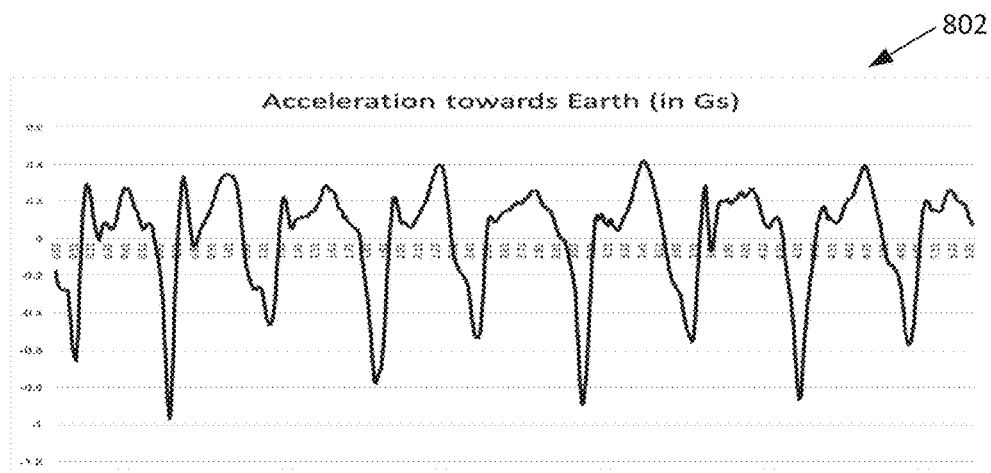
FIG. 8A shows a graphical representation of an example raw accelerometer information that was recorded while a user was walking.

Referring now to FIG. 8A, which shows a graphical representation 802 of example raw accelerometer information that was recorded while a user was walking. In particular, it shows sample user earth y axis (earth coordinate system) acceleration showing periodicity. As you can see, the regular peaks represent each step that the user takes. In this example of a person's movement associated with walking, a variety of vector calculations on this window can be done in order to determine the "features" of the signal. Some descriptions of these algorithms/calculations can be found, for example, at a library located at http://tsfresh.readthedocs.io/en/latest/text/list_of_features.html—known as tsfresh.

In some embodiments, the "maximum" feature returns the maximum acceleration signal in the 2s window. Based on past modeling efforts and experimentation, it is clear that a fall tends to have a higher overall maximum acceleration value than normal, relative to day-to-day data. Experiments like this, as well as p-value statistical relevance calculations (and the Mann-Whitney U test for determining relative significance between features—see https://en.wikipedia.org/wiki/Mann%E2%80%93Whitney_U_test), is how the optimal set of features as shown in FIG. 8B, which is an example list of feature values, may be calculated for a windowed sensor data according to some embodiments. FIG. 8B shows sample window feature calculations 810 (performed on multiple sensor inputs).

Each feature value may then be independently normalized by subtracting its mean (resulting in a mean of 0) and scaling it to a variance and standard deviation of 1. This has two key benefits:

1. The standard deviation value is a better "score" for the feature than the raw value. In the training data that are to be used, there may be, for example, 100,000 motion samples of people washing their hands. Feature calculations on those samples can be expected to be normally distributed around the mean (that is, the right value on average may be found, and sampling errors may be distributed normally), and what is important is how "anomalous" a new sample is, not the absolute value of a specific equation.
2. Generally avoids large raw values from dominating the training.

Figure 9A:
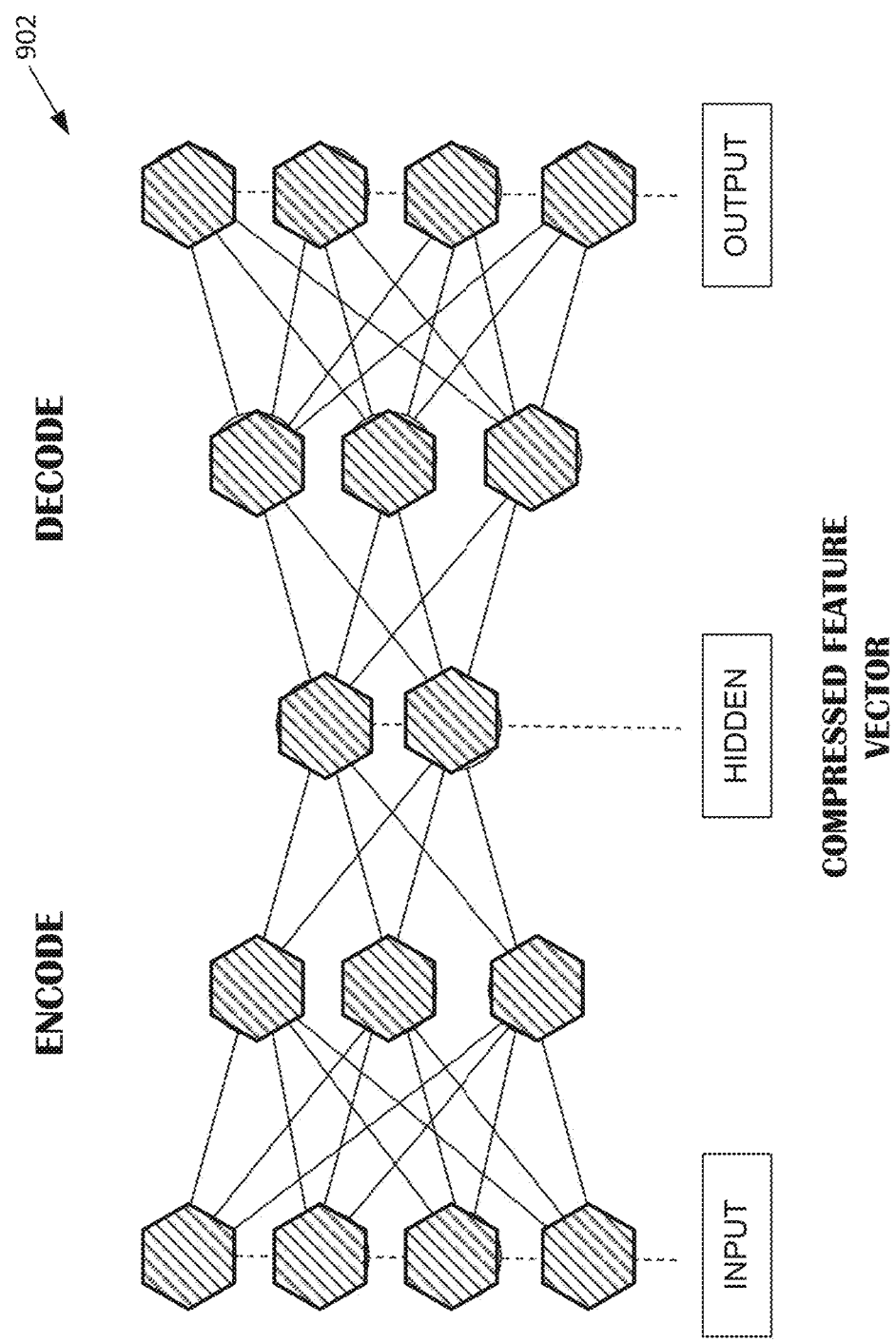
FIG. 9A is an example visual high-level representation of a type of Neural Network known as Autoencoder.

Turning now to FIG. 9A, which is an example visual, high-level representation 902 of a type of Neural Network known as an Autoencoder. More particularly, it shows a sample auto-encoder model representation. Note that this diagram is not meant to literally represent the neural networks employed by the personalized ML networks previously described. Instead, it is just a high-level conceptual diagram of one type of neural network that may be employed and to make the discussion below easier to understand.

Figures 9B, 9C:
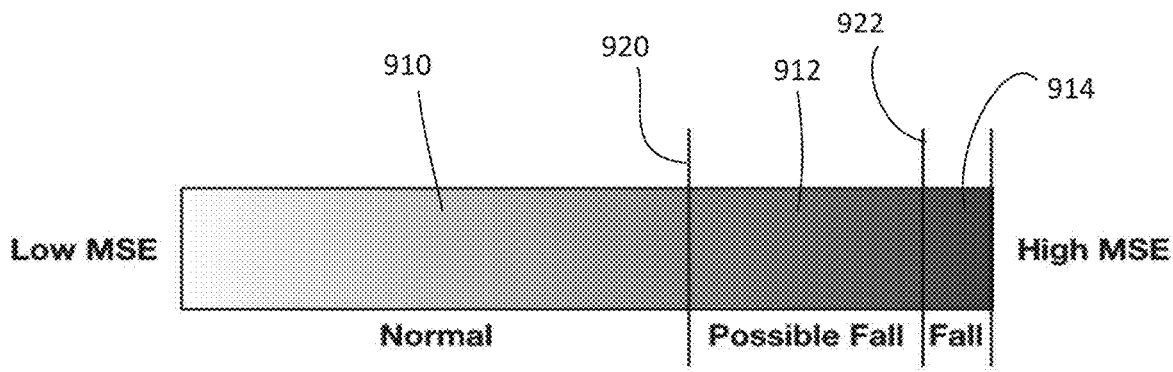
FIG. 9B shows details of example Autoencoder layers.
FIG. 9C illustrates example normal activity anomaly bands.

In some embodiments, the ADNN is a nine-layer Autoencoder as illustrated in FIG. 9B. More particularly, FIG. 9B shows details of example Autoencoder layers 904 (i.e. "shape"). It has an input layer and then eight Fully-Connected Layers. The Output Shape column shows the # of neurons in that layer. The Param # shows the number of weights learned for that layer. More details will herein be provided below. Note that in alternative embodiments, the ADNN may be an Autoencoder with other number of layers.

The input is the vector of normalized feature values (1×338) from the Feature Calculation step. The output is an identically shaped vector of values (1×338). The mean squared error (MSE) of these two vectors is how anomalous the original signal is from a normal, day-to-day activity signal. The higher the MSE, the more likely it's a fall. Note that if Y is a vector of n predictions, and Y is the vector of observed values corresponding to the inputs to the function which generated the predictions, then the MSE of the predicator can be estimated by:

$$MSE = \frac{1}{n}\sum_{i=1}^{n}\left(\hat{Y}_i - Y_i\right)^2$$

Alternate error functions like cross-entropy could be used in place of MSE.

FIG. 9C illustrates normal activity anomaly bands 910, 912, and 914 that are separated by threshold lines 920 and 922 and that indicates possible falls. It also shows how the MSE value may dictate whether a fall is detected or not detected:

Low MSE (MSE<Possible Fall threshold)
    Regular activity, not a fall
Medium MSE (Possible Fall threshold<MSE<Fall threshold)
    Possible fall. Less urgency in the UI to alarm.
High MSE (Fall threshold<MSE)
    Fall. Alarm is more likely to fire and is more urgent.

Note that the threshold lines 920 and 922 may move left or right depending on the activity level of the user. For example, if the user is more active, then the threshold lines 920 and 922 will likely move to the right. If, on the other hand the user is less active then the threshold lines 920 and 922 will likely move to the left.

In various embodiments, the FS systems and methods may find anomalous conditions when the MSE value is high. An anomaly is a possible fall. Note that the possible fall range may have a different user experience.

Using various personalization techniques described herein, the Fall Threshold values (e.g., threshold lines 920 and 922) may be changed for each user, resulting in more accurate fall detection on a personalized basis.

Training

So how is the ADNN (e.g., personalized ML model), the nine-layer Autoencoder, trained? An Autoencoder is: "an autoencoder is a feedforward, non-recurrent neural network very similar to the multilayer perceptron (MLP)—having an input layer, an output layer and one or more hidden layers connecting them —, but with the output layer having the same number of nodes as the input layer, and with the purpose of reconstructing its own inputs (instead of predicting the target value Y given inputs X."

In short, an Autoencoder is a neural network that tries to exactly reproduce the input signal in the output signal. It "auto-encodes" itself; that is, it "creates a code to efficiently represent itself." In some ways, it can be thought of like a data compression engine.

The models that the FS systems use, for example, learns how to recreate any normal set of feature values from the 25 neurons in the center of the model. Think of the 25 middle neurons as "meta-features," the key signatures of regular activities. So when a fall signal is fed to one of the models, it has difficulty recreating it accurately. That's why the Mean Squared Error (MSE) is high, and a fall can be detected.

So how is the ADNN trained?

Normal data is fed into the ADNN and a determination is made as to how well it recreates that same data. By looking at the error of reconstruction, back-propagate changes to the weights of each neuron's inputs may be performed. Over millions of training windows, the Autoencoder learns a set of weights that properly re-creates normal data, but (intentionally) has trouble reproducing fall data.

There are a number of ways the FS systems may collect data needed to develop and train generic ML models that may be employed in various alternative embodiments. One approach is to have volunteers with smartphones (and optionally, connected wearable devices) running a data gathering application, which may be specifically designed for this purpose, performing a variety of activities in the same context as the target demographic, including walking, jogging, going up or down flights of stairs, sitting down abruptly, etc. The data gathering application may record a number of acceleration, device orientations, heart rate, and other parameters several times a second. In some embodiments, the FS systems (e.g., the model management system 12 of FIGS. 1A, 1B, 1C, and 1D) may collect this data during the activities (which could provide well over 10,000 rows of data for a few minutes of data) and may upload it to a cloud data store.

Clearly, the FS systems cannot have volunteers go through serious falls, slips or trips. To get log data for such situations, the FS systems may employ a humanoid dummy carrying smartphones and smartwatches with the same data gathering application. Wherever possible, the FS systems may also video activities of a demographic group such as the elderly, so that the context of the data is better understood for analysis. After each activity, the FS systems and methods may upload the numerical data, along with the video data, for later analysis. The advantage of this method is that the data can be reasonably well-labeled because the data gathering will be done under controlled conditions.

In some embodiments, the data may be collected is by logging data from actual users or beta testers testing the FS systems (e.g., model management system 12, the training system 14\*, and the fall detection engine 16\*). When at least one of the FS systems (e.g., fall detection engine 16\*) indicates it has detected a fall, the FS systems may collect the last few minutes of buffered acceleration and device orientation, heart rate, and other data, and upload it to a cloud data store. Wherever feasible, the user may be requested to label the fall as a real fall, or as a false alarm, along with a description of the associated activity. In various embodiments, the monitored senor data may be sampled every few minutes to help compute a personalized baseline for each user.

In addition, the real world has far more variations of circumstances which may lead to a larger set of fall scenarios and incidents. Data logging helps the FS systems collect data for these scenarios and incidents.

In some cases, rather than using real world data, the FS systems may employ virtual world data or computer simulation data. Virtual worlds with rag doll dummies (3D modeled humanoids with realistic movement) may be used to simulate a large number of activities including normal activities and anomalous activities including falls. The potentially large amount of fall data from a realistic virtual world may help the training and detecting of more scenarios of normal activity and of anomalous activity.

Data Augmentation and Feature Engineering

In one phase, the FS systems may work with the recorded features in a First Principles Method to get to parameters or features which may help model the fall detection problem best. The goal here is to be principled about features that may be added.

In augmentation, for example, the FS systems may compute and add as features the first and second derivatives of acceleration (jerk and jounce, respectively). The FS systems may look at time-windows of data and add statistical measures over the data. The FS systems may also choose to normalize or scale the data to better apply various data techniques. Feature engineering may also involve data exploration with graphing or trying out correlations (for example) to prune out redundant features. The FS systems may use signal processing tools such as spectral power density estimation and binning to bring additional discriminatory features to bear upon the problem.

At the end of these steps, the FS systems may have data which can be fed to one or more machine learning algorithms to model the fall detection problem. Once the FS systems has a model, the FS systems can run test data on it, iterate through this process of collecting data, cleaning and augmenting it, modeling the problem, and testing it. Once there is an acceptable level of accuracy in detecting falls, trips and slips, along with a low incidence of false alarms, the FS systems can deploy the solution to real users.

The data logging from real users may help the FS systems personalize and refine the machine learning model. With use, there may be significant user-specific data that is collected. That can help refine the baseline and do a better job of detecting anomalous situations that need to be handled, and personalize it to the specific users contributing the logs, forming a virtuous feedback cycle.

System Technical Overview

According to various embodiments, an end-to-end system is provided herein to provide personalized fall detection for various demographic groupings including, for example, the elderly and infirm. The fall detection algorithm may be created using signal processing with machine learning techniques and the training of the machine learning model will take place using cloud-based computing. The machine learning model and associated runtime/decision tree may then be run on a mobile device (e.g., smartphone device or smartwatch device). This may help lower the cost (and increase potential adoption) of the fall detection solution by leveraging the mobile devices that most of the general population already have.

A quick overview of the FS systems can be described as having three general phases:

1. A generalized, pre-trained machine learning model is used to detect falls for the elderly and infirm.
2. A system is used to receive and process feedback in the form of user generated content when a false alarm is reported. This system is used to create an updated, personalized machine learning model for each user.
3. An updated, personalized machine learning model is used to detect falls more accurately for an individual.

Referring to FIGS. 10A, 10B, 10C, 10D, 10E, 10F, and 10G illustrate how a mobile device client application is provisioned with an updated personalized ML model in accordance with various embodiments of the present disclosure. Turning particularly now to FIG. 1A, which shows a mobile device application 1002 running a pre-trained machine learning model to provide fall detection for a segment of the general population such as the elderly and infirm. Note: The pre-trained machine learning (ML) model and runtime are part of the mobile solution running on the mobile device. It wasn't until recently that methods for running machine learning models have become available for popular mobile device platforms like ANDROID, IOS, and WATCHIOS.

Figure 10A:
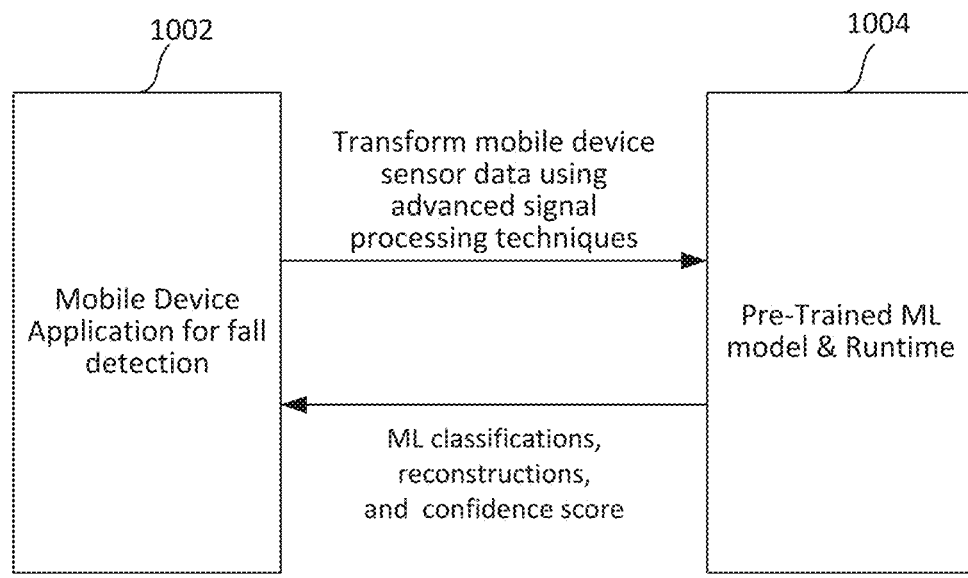
FIGS. 10A, 10B, 10C, 10D, 10E, 10F, and 10G illustrates how a mobile device client application is provisioned with an updated personalized ML model in accordance with various embodiments.

In any event, and as illustrated in FIG. 10A, the mobile device application 1002 may transform user sensor data using advanced signal processing techniques and provide the processed user sensor data to the pre-trained ML model & runtime 1004. The ML model & runtime 1004 may then provide to the mobile device application 1002 ML classifications, reconstructions, and confidence score. Note that in some cases, the pre-trained ML model & runtime 1004 may also reside at the mobile device.

Figure 10B:
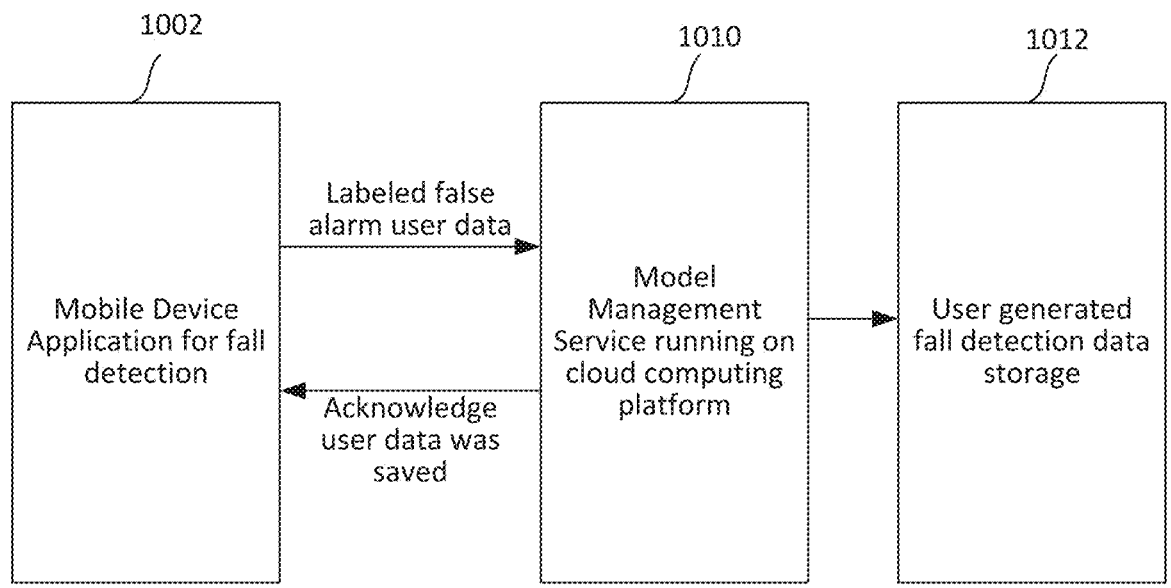

Referring to FIG. 10B, which shows that a person can opt-in to personalize their fall detection, sharing their labeled sensor data by uploading it to a fall detection service 1022. This service stores the data to be used for personalizing fall detection for the individual and to improve the pre-trained ML model as shown in FIG. 10A.

In the embodiment illustrated in FIG. 10B, the mobile device application 1002 provides to the model management service 1010, which may be running on cloud computing platform, user sensor data that is labeled as a false alarm. That is, the user sensor data may have been initially detected as being an anomaly, but having been determined to be associated with a non-fall event rather than a fall event, and is, therefore, now labeled as a "false alarm." In response, the model management service 1010 saves user generated fall detection data (e.g., user sensor data labeled as false alarm) to, for example, storage (e.g., data store). The model management service 1010 may also send an acknowledgement back to the mobile device application 1002 that acknowledges that the user sensor data was saved.

Figure 10C:
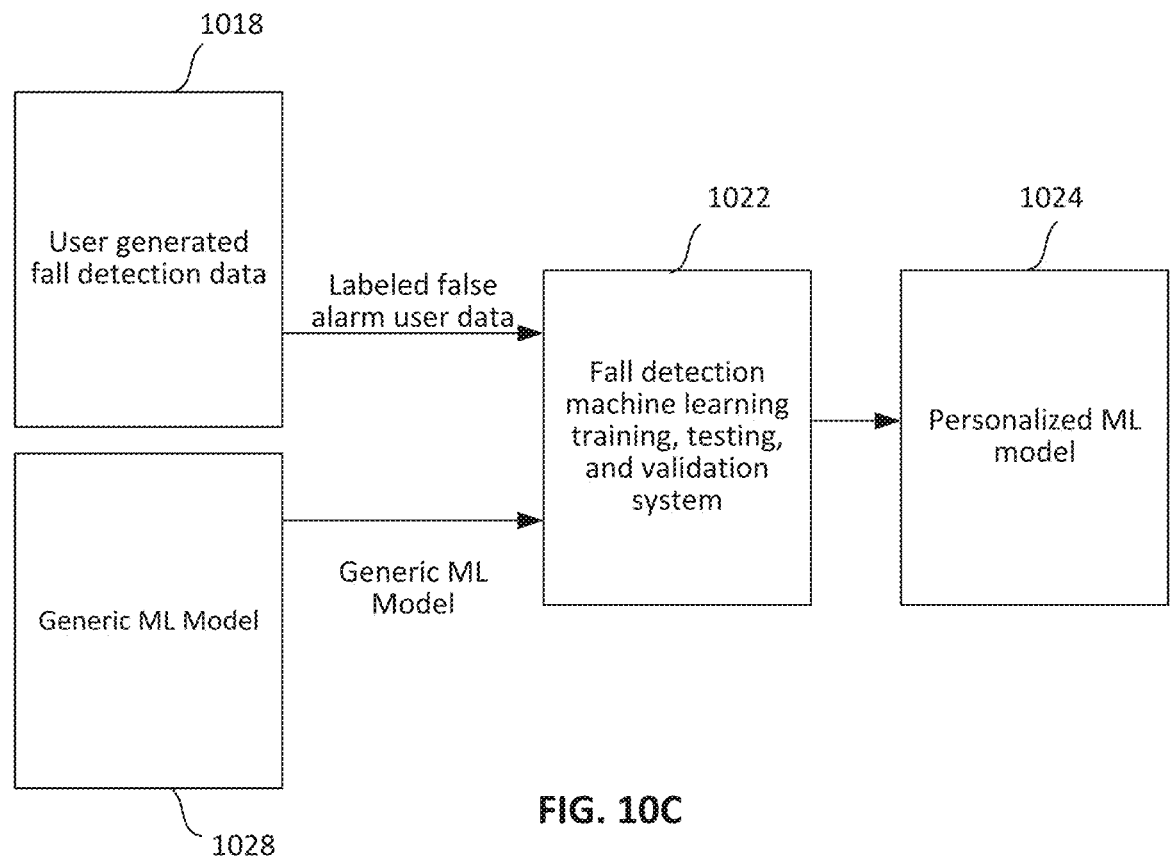

Turning now to FIG. 10C, which shows the combination of user generated data (e.g., user sensor data) with a generic ML model being fed into the machine learning training, testing, and validation part of the FS systems to create a personalized (and therefore more accurate) ML model for the individual based on their specific feedback.

In FIG. 10C, a labeled false alarm user data is provided to a fall detection machine learning, training, testing, and validation system 1022, where the labeled false alarm user data was generated based on the user generated fall detection data 1018. The fall detection machine learning, training, testing, and validation system 1022 may also be provided with labeled true fall or false alarm control data generated from general fall detection data 1028. The fall detection machine learning, training, testing, and validation system 1022, in response, provides a personalized ML model 1024. Note that in alternative embodiments, rather than combing user generated data with a generic ML model to create the personalized ML model, the user generated data may be combined with sensor data collected from multiple users to generate personalized ML model as illustrated in FIG. 10G. The sensor data collected from multiple users may include sensor data associated with false alarm events (e.g., non-fall events).

Figure 10D:
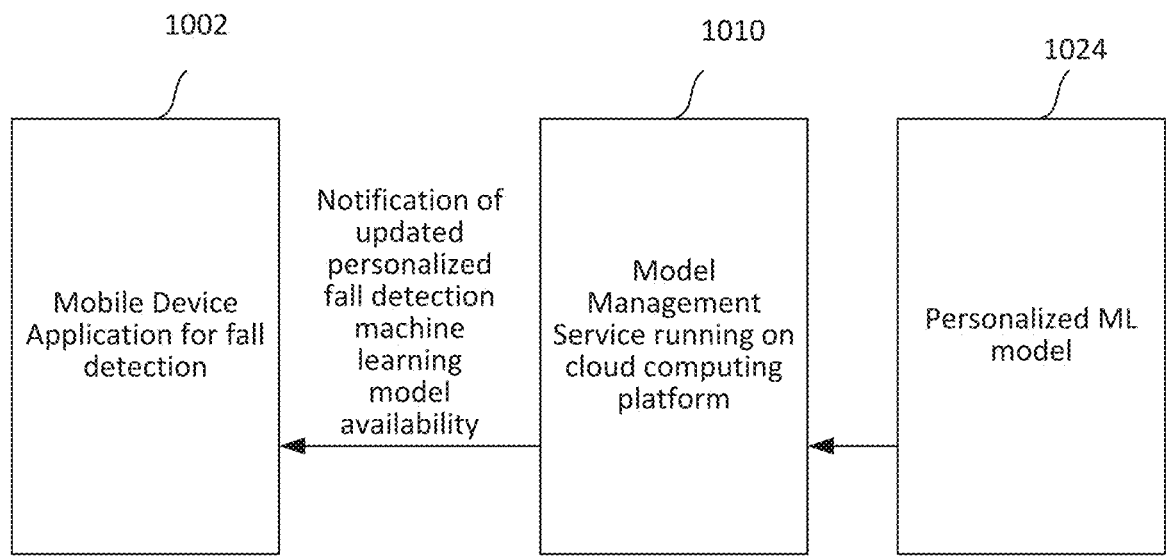

FIG. 10D shows that when the updated, personalized machine learning model 1024 is ready, the mobile device application 1002 is notified about the available update by the model management service 1010.

Figure 10E:
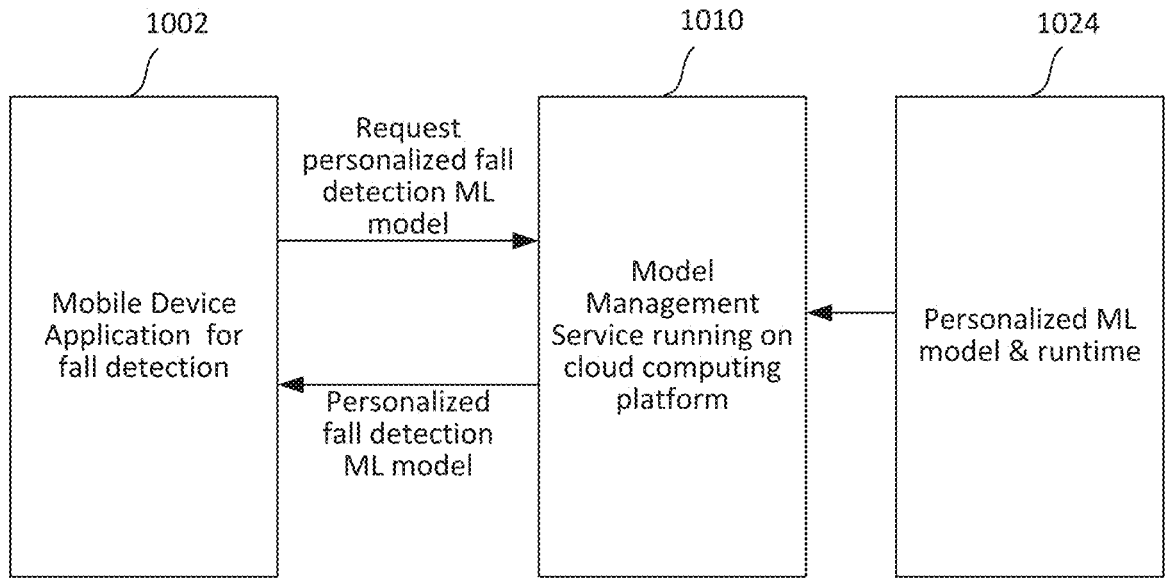

FIG. 10E shows the mobile device application 1002 requesting the updated, personalized ML model & runtime 1024 and replacing on the mobile device the original, pre-trained ML model 1004, or an older version of their own personalized ML model for fall detection.

Figure 10F:
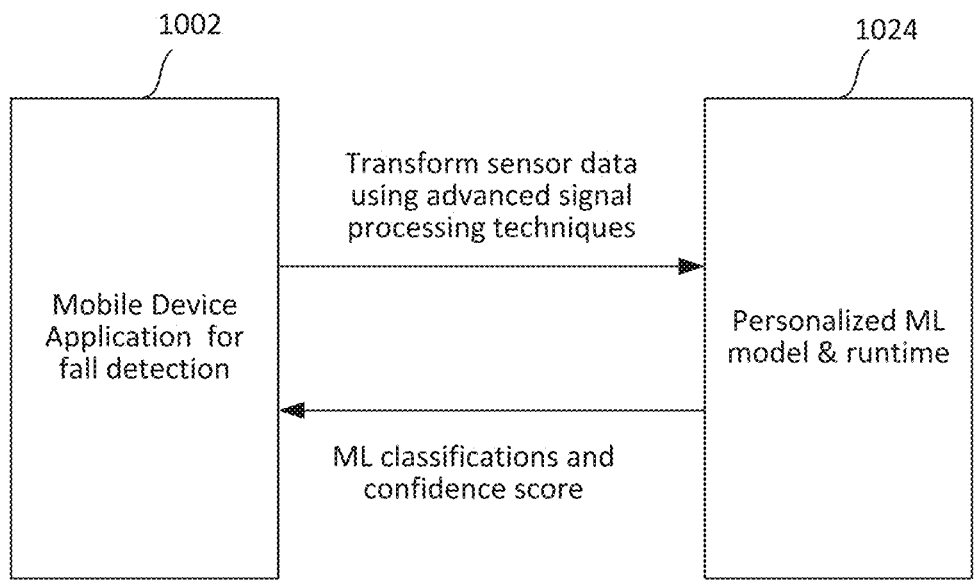
Figure 10G:
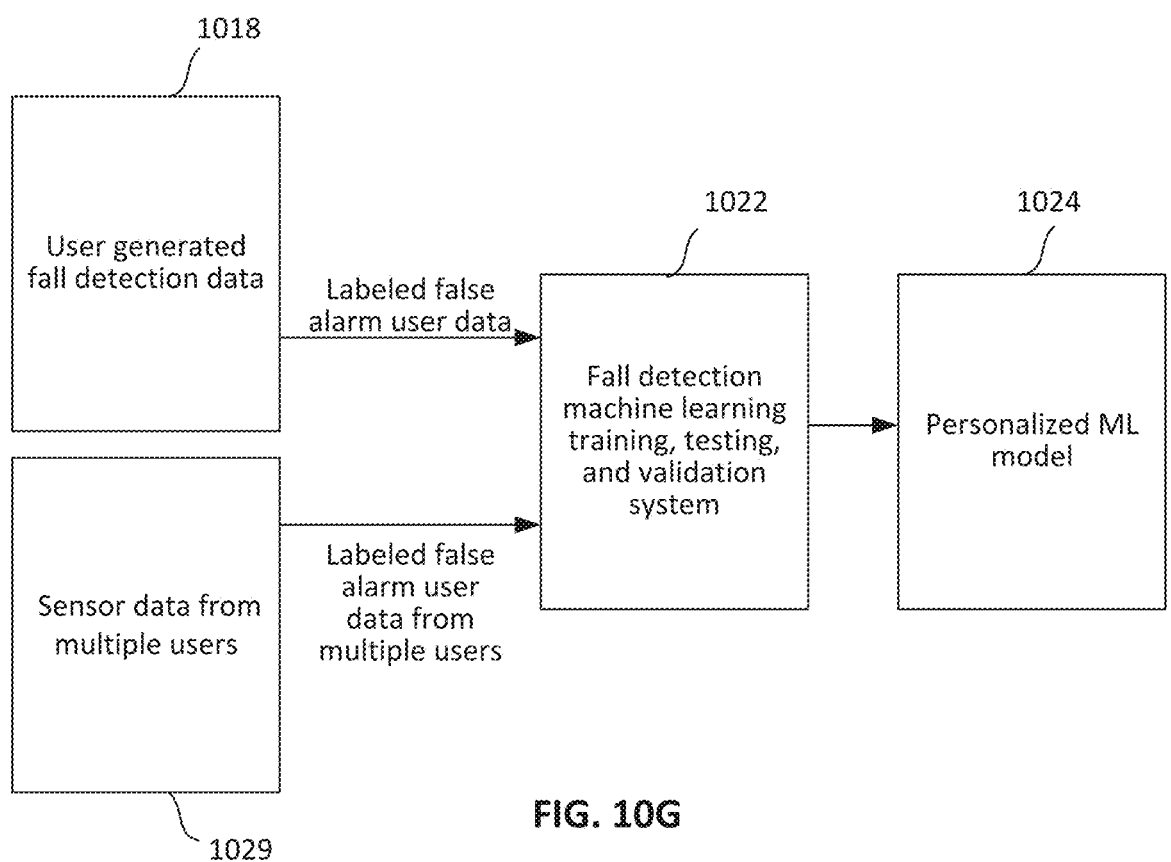

FIG. 10F shows he mobile device application 1002 now running the updated, personalized ML model & runtime 1024.

Detecting Human Self-Defense Motions

In many cases, when a human is falling in a way that is harmful, he will naturally try to protect himself. For example, if you trip, you put your arms out to avoid falling on your face. Using sensor in a mobile device or a dedicated device, especially a wearable device such as a smartwatch, which is worn on the wrist, we can detect this "human self-defense" motion. This may help us differentiate between a real fall and jumping into your bed, where the human doesn't guard himself against the bed.

Anomaly Detection

Many Artificial Intelligence (Machine Learning) algorithms attempt to classify data into groups. A well-known example is GOOGLE's image classifier (a Deep Convolutional Neural Network) for GOOGLE PHOTOS. By taking labeled images of different objects (e.g. pictures of cats & dogs from GOOGLE's search engine) & sending the raw pixels into this classifier, it is able to reliably learn the difference between a cat, a dog, a rabbit, a tree, etc.

For fall detection, well-known Machine Learning algorithms like the Deep Convolutional Neural Network may be used. That said, a novel method is employed that greatly increases the accuracy of our ML.

Unlike classifying the names of objects seen in images, in fall detection only about two activity classes may be relevant: 1) normal activity, which happens 99.9% of the time, and 2) falls, which rarely occur. We found that we greatly increased the accuracy of our AI by only training on normal activity. Here's why:

Falls are so rare that training our AI (e.g., ML model) to only look for one "anomaly case" increased its accuracy. The AI that may be employ doesn't have to "waste neurons" learning the difference between cooking, walking, dancing, eating, etc. It is specialized to find rare, dangerous falls.

It's easy to collect training data for normal activity. Therefore, hundreds of millions of sensor data points may be collected, which greatly improved the AI.

In order to create generic ML models, an application was developed and participants were recruited who wanted to help with fall prevention and protection. Each participant ran the application in the background on their mobile devices to provide training data.

Height Detection

According to various embodiments, the FS systems use the accelerometer and gyroscope sensors of the mobile devices that users possess or wear (e.g. smartphone, smartwatch, etc.). Having both sensors allows the mobile device, or at least client application running on the mobile device, to determine the direction of gravity, which permits the user's acceleration towards Earth to be detected.

Using basic physics, we then integrate the acceleration function a(t) over time t to calculate the velocity function v(t). We assume the initial velocity v0 is 0 m/s towards earth since the user has not started falling.

We then integrate the velocity function v(t) over time t to calculate the vertical position function r(t). The change in vertical position tells us how far the person fell, which is one of the signals we use to accurately detect falls. In particular, the equations below may be used in order to determine how far a person has fallen:

| | Derivative Form | Integral Form |
|---|---|---|
| Position | $r(t)$ | $r(t) = r_0 + \int_0^t v\,dt^1$ |
| Velocity | $v(t) = \dfrac{dr}{dt}$ | $v(t) = v_0 + \int_0^t v\,dt^1$ |
| Acceleration | $a(t) = \dfrac{dv}{dt} = \dfrac{d^2 r}{dt^2}$ | $a(t)$ |

Body Detection

According to various embodiments, the FS systems and methods are able to detect between two cases that initially might seem ambiguous:

1) Putting your iPhone on the table
2) Lying unconscious with the iPhone in your pocket This provides another signal that can be used to reliably detect falls. Two techniques can be used to do this:

Determining the absolute rotational position of the device, so we know if the device is lying at an angle in the person's pocket (likely), or very flat like on a table.

Detecting the human

Proximity Sensor—the same sensor that's used by the mobile to turn off the touchscreen when you place your face next to it to make a phone call "Breathing" detection. The phone moves slightly with a pattern when touching a breathing human as opposed to sitting on a table.

Heart rate—we can detect the human's pulse

Personalized Fall Detection

In various embodiments, the FS systems are able to personalize its fall detection algorithms to each user. This increases the accuracy, since an activity that looks like a fall for one user might be a common, normal activity for another. Here is how we personalize the fall detection:

User's Health

When available, we ask for demographic information about the user. For example, older women have different behavior patterns from younger men.

When available, the FS systems can query the user's mobile device for health information. For example, APPLE devices provide HEALTHKIT, which automatically tracks health & fitness data. From this, the FS systems can distinguish between an active hiker like Stacy and the more stationary man Joe from the scenarios above.

Direct user feedback

If the FS systems incorrectly detects a fall, and the user cancels the alarm, the FS systems can use that information to reduce false alarms for that user.

In addition, by sending this information to our central cloud storage, we're able to use that signal to improve our algorithms for other, similar users.

Individual usage patterns

The FS systems can automatically learn from each user's motion patterns. For example, if a user exercises every morning, the FS systems can learn that pattern and can tune fall detection to reduce false alarms Referring to FIG. 11, which illustrates three example screen shots 1102, 1104, and 1106 in accordance with various embodiments of the present disclosure. In various embodiments, the screen shots 1102, 1104, and 1106 may be displayed by an end user device 20*. In various embodiments, screen shot 1102 may be initially displayed when the FS client application residing at the end user device 20* has been activated. As illustrated, screen shot 1102 indicates that the FS client application residing at the end user device 20* is activated and is monitoring activities of the user 22. Screen shot 1102 also includes a panic button 1120 that generate an alert to one or more contact for emergency situations.

In some embodiment, screen shot 1104 may be displayed by the end user device 20* when, for example, a fall event has been detected. The screen shot 1104 includes a countdown window 1140 that indicates how much time the user has left to cancel the alarm. If the user 22 fails to cancel the alarm, then at the end of the countdown, an alert may automatically be sent to one or more emergency contacts. The screen shot 1104 further includes a cancel button 1142 for cancelling the alarm.

Figure 11:
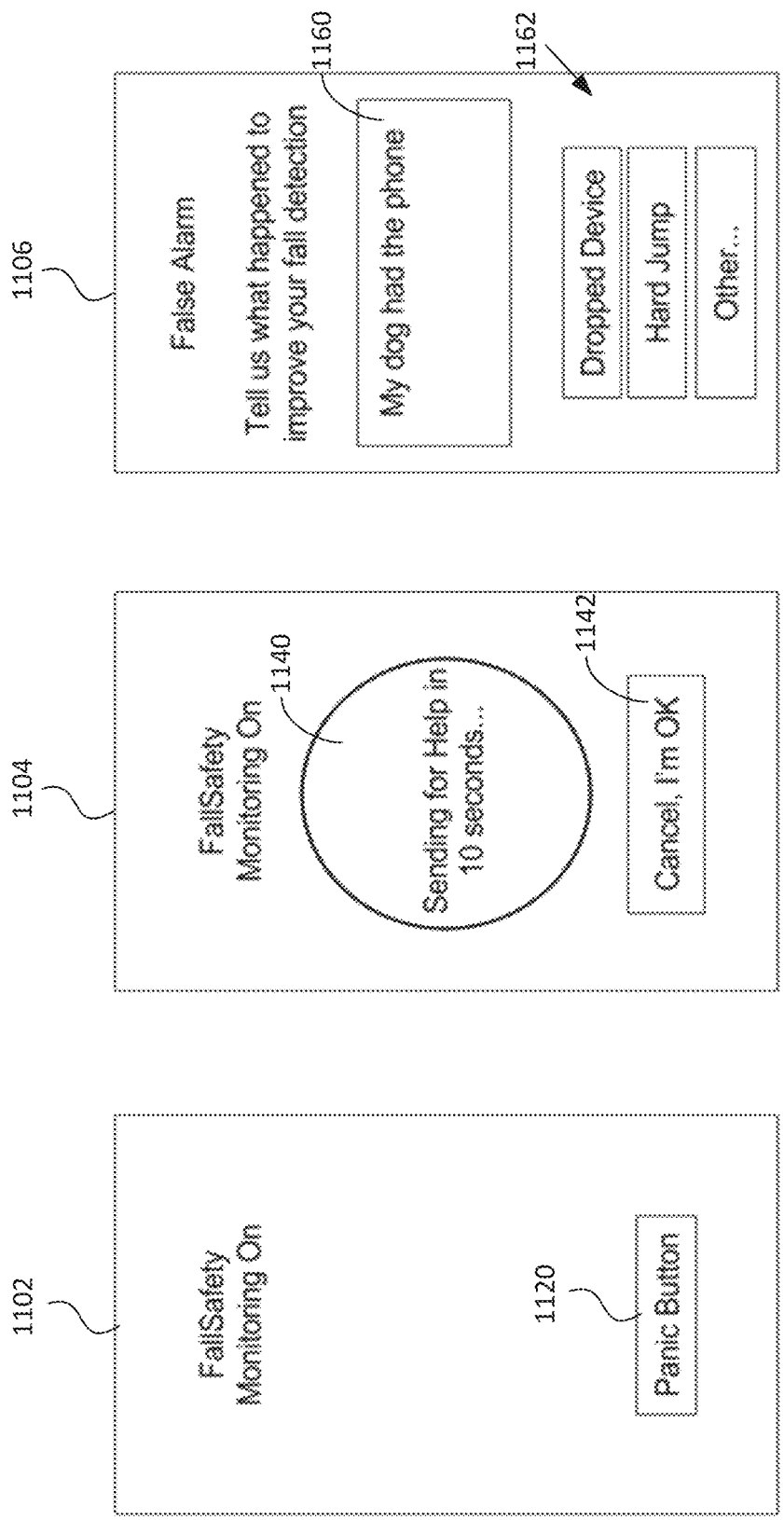
FIG. 11 shows three example screen shots at three different stages of detection of a false alarm fall event according to some embodiments

In contrast to screen shot 1104, screen shot 1106 may be displayed by an end user device 20* when a false alarm event (e.g., a non-fall event that is not initially recognized by a personalized ML model, but subsequently confirm to be a non-fall event) has been detected. The screen shot 1106 is designed to allow the user 22 to label the false alarm event. In some embodiments, the screen shot 1106 may include a window 1160 that permits the user 22 to write a label for the false alarm event. The screen shot 1106, as illustrated in FIG. 11, may also include pre-set label buttons that the user 22 may simply press/click.

After reviewing the present disclosure, an individual of ordinary skill in the art will immediately appreciate that some details and features can be added, removed and/or changed without deviating from the spirit of the invention. Reference throughout this specification to "one embodiment," "an embodiment," "additional embodiment(s)" or "some embodiments," means that a particular feature, structure or characteristic described in connection with the embodiment(s) is included in at least one or some embodiment(s), but not necessarily all embodiments, such that the references do not necessarily refer to the same embodiment(s). Furthermore, the particular features, steps, structures, or characteristics may be combined in any suitable manner in one or more embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

What is claimed is:

1. A computer implemented method for detecting fall events of a user using a personalized machine learning (ML) model, comprising:

obtaining sensor data associated with one or more activities of the user, the personalized ML model designed to recognize processed sensor data associated with non-fall activities, a copy of the sensor data having been previously processed and the previously processed sensor data having been fed to the personalized ML model, the obtained sensor data being determined to be associated with an anomalous event when the personalized ML model does not recognize the previously processed sensor data, and the anomalous event determined not to be associated with a fall event without confirmation from the user that the anomalous event was not associated with a fall event and following determination that the obtained sensor data was associated with an anomalous event;

training, in response to determining that the anomalous event was not associated with a fall event, the personalized ML model using the sensor data; and providing the trained personalized ML model to determine occurrence of a fall event involving the user.

2. The computer implemented method of claim 1, wherein determining that the previously processed sensor data is not associated with a fall event is based, at least in part, on the sensor data.

3. The computer implemented method of claim 1, wherein the determination that the previously processed sensor data is not associated with a fall event is by parsing data collected before or after occurrence of the anomalous event.

4. The computer implemented method of claim 3, wherein the parsing of data collected before or after occurrence of the anomalous event includes inferring that the anomalous event was not a fall event based on data collected after occurrence of the anomalous event that indicates movements of the user after the occurrence of the anomalous event.

5. The computer implemented method of claim 1, further comprising:
obtaining other sensor data associated with other one or more activities of the user, the other sensor data being determined to be associated with another anomalous event when the personalized ML model does not recognize processed sensor data of the other sensor data;
determining that the another anomalous event is a fall event; and
determining confidence level that the another anomalous event was a fall event.

6. The computer implemented method of claim 5, wherein if the confidence level is low confidence that the another anomalous event was a fall event then providing an option to the user to confirm or cancel an alert to be sent to one or more emergency contacts and which is automatically cancelled if the user does not confirm occurrence of the fall event within a predefined period of time, wherein if the confidence level is medium confidence that the another anomalous event was a fall event then providing an option to the user to cancel within a predefined period of time an alert to be sent out to the one or more emergency contacts and if the user does not cancel within the predefined period of time then the alert is automatically sent to the one or more emergency contacts, and wherein if the confidence level is high confidence that the another anomalous event was a fall event then automatically sending an alert to the one or more emergency contacts without giving the user an option to cancel the sending of the alert.

7. The computer implemented method of claim 5, wherein the determination of the confidence level is based, at least in part, on vertical movement of the user during the fall event indicated by the other sensor data.

8. The computer implemented method of claim 1, wherein training the personalized ML model using the sensor data includes:
extracting relevant data from the sensor data to provide windowed data;
calculating feature values on the windowed data; and
training the personalized ML model using the calculated feature values.

9. The computer implemented method of claim 1, wherein providing the trained personalized ML model including transmitting the trained personalized ML model to a mobile computer device associated with the user.

10. The computer implemented method of claim 1, further comprising:
detecting an anomalous event using the trained personalized ML model; and
determining occurrence of a fall event based, at least in part, on the detection of the anomalous event.

11. The computer implemented method of claim 10, wherein determining the occurrence of the fall event includes determining that distance traveled towards earth by one or more sensors that provided the sensor data exceeds a threshold distance.

12. One or more non-transitory computer readable media having stored thereon instructions, that when executed by one or more processors of a computer system, cause the computer system to perform operations for detecting fall events of a user using a personalized machine learning (ML) model comprising:
obtaining from one or more sensors of a mobile computing device sensor data associated with one or more activities of a user, the personalized ML model designed to recognize processed sensor data associated with non-fall activities, a copy of the sensor data having been previously processed and the previously processed sensor data having been fed to the personalized ML model, the obtained sensor data being determined to be associated with an anomalous event when the personalized ML model does not recognize pattern of the previously processed sensor data, and the anomalous event determined not to be associated with a fall event without confirmation from the user that the anomalous event was not associated with a fall event and following determination that the obtained sensor data was associated with an anomalous event;
training, in response to determining that the anomalous event was not associated with a fall event, the personalized ML model using the sensor data; and
provisioning the mobile computing device with the trained personalized ML model to determine occurrence of a fall event involving the user.

13. The one or more non-transitory computer readable media of claim 12, wherein the sensor data is obtained from the mobile computing device via one or more networks.

14. The one or more non-transitory computer readable media of claim 12, wherein the personalized ML model is a personalized normal activity ML model.

15. The one or more non-transitory computer readable media of claim 12, wherein the personalized ML model is configured as an autoencoder neural network, a Long Short-Term Memory (LSTM) network, a multiple linear regression model, or a random forest classifier.

16. The one or more non-transitory computer readable media of claim 12, wherein the personalized ML model includes a generalized normal activity ML model generated using activity data of members of a segment of general population and a personalized normal activity ML model generated using activity data of the user, the generalized normal activity ML model and the personalized normal activity ML model being chained together in an ensemble fashion.

17. The one or more non-transitory computer readable media of claim 12, wherein the personalized ML mode is generated by combining a generalized normal activity ML model that was generated using activity data of members of a segment of general population and a personalized normal activity ML model that was generated using activity data of the user.

18. The one or more non-transitory computer readable media of claim 12 wherein training the personalized ML model using the sensor data includes:
extracting relevant data from the sensor data to provide windowed data;
calculating feature values on the windowed data; and
training the personalized ML model using the calculated feature values.

19. The one or more non-transitory computer readable media of claim 12, wherein determining that the previously processed sensor data is not associated with a fall event is based, at least in part, on the sensor data.

20. A system, comprising:
at least one memory configured to store computer-executable instructions;
at least one processor configured to access the at least one memory and execute the computer-executable instructions to:
obtain sensor data associated with one or more activities of a user, at least a copy of the sensor data having been fed to a personalized ML model of the user, the personalized ML model designed to recognize sensor data associated with non-fall activities of the user, the obtained sensor data being determined to be associated with an anomalous event when the personalized ML model does not recognize the at least the copy of the sensor data, and the anomalous event determined not to be associated with a fall event without confirmation from the user that the anomalous event was not associated with a fall event and following determination that the obtained sensor data was associated with an anomalous event;

train, in response to determining that the anomalous event was not associated with a fall event, the personalized ML model using the sensor data; and provide the trained personalized ML model to facilitate determination of an occurrence of a fall event involving the user.

\* \* \* \* \*